United States Patent
Hsu et al.

(10) Patent No.: US 9,241,613 B2
(45) Date of Patent: Jan. 26, 2016

(54) DEVICES AND METHODS FOR CLOSURE OF WOUNDS

(75) Inventors: Thomas Hsu, Foster City, CA (US); Senzan Hsu, Foster City, CA (US)

(73) Assignee: MEDEON BIODESIGN, INC. (TW)

( * ) Notice: Subject to any disclaimer, the term of this patent is extended or adjusted under 35 U.S.C. 154(b) by 664 days.

(21) Appl. No.: 12/663,579

(22) PCT Filed: May 31, 2008

(86) PCT No.: PCT/US2008/006924
§ 371 (c)(1),
(2), (4) Date: Dec. 8, 2009

(87) PCT Pub. No.: WO2009/002390
PCT Pub. Date: Dec. 31, 2008

(65) Prior Publication Data
US 2010/0185217 A1    Jul. 22, 2010

Related U.S. Application Data

(60) Provisional application No. 60/933,693, filed on Jun. 8, 2007.

(51) Int. Cl.
*A61B 17/04* (2006.01)
*A61B 1/012* (2006.01)
*A61B 1/00* (2006.01)
*A61B 1/12* (2006.01)
*A61B 1/313* (2006.01)

(52) U.S. Cl.
CPC .............. *A61B 1/012* (2013.01); *A61B 1/00087* (2013.01); *A61B 1/00135* (2013.01); *A61B 1/126* (2013.01); *A61B 1/3132* (2013.01); *A61B 1/00142* (2013.01)

(58) Field of Classification Search
CPC .......... A61B 17/0469; A61B 17/0482; A61B 2017/0472; A61B 2017/00637
USPC .......................... 606/139, 144, 148; 112/169
See application file for complete search history.

(56) References Cited

U.S. PATENT DOCUMENTS

| 3,145,249 A | 8/1964 | Meltzer |
| 5,041,129 A | 8/1991 | Hayhurst et al. |

(Continued)

FOREIGN PATENT DOCUMENTS

| EP | 0648044 A1 | 10/1997 |
| GB | 2188746 A | 10/1987 |

(Continued)

*Primary Examiner* — Alexander Orkin
(74) *Attorney, Agent, or Firm* — Dergosits & Noah LLP; Todd A. Noah

(57) ABSTRACT

The invention encompasses devices and methods used to provide wound closure based on rings positioned within the tissue layers of the wound opening (with the rings regionally separate the wound depth tissue layers into 2 compartments), followed by suture transport through the rings and full-thickness tissue layers of both compartments. Upon suture transport via synchronous or asynchronous manner and device removal, wound closure is achieved by tying the 2 ends of the suture without incorporating tissue above the level of the rings such as skin. When the device is applied to abdominal or chest wall wound opening, all tissue layers except the skin are incorporated in the suture closure of the wound. The closure process can be performed in a simple, reliable, and expeditious manner.

18 Claims, 16 Drawing Sheets

(56) References Cited

U.S. PATENT DOCUMENTS

| | | |
|---|---|---|
| 5,085,661 A | 2/1992 | Moss |
| 5,149,329 A | 9/1992 | Richardson |
| 5,217,486 A | 6/1993 | Rice et al. |
| 5,222,508 A | 6/1993 | Contarini |
| 5,281,234 A | 1/1994 | Wilk et al. |
| 5,281,237 A | 1/1994 | Gimpelsom |
| 5,320,629 A | 6/1994 | Noda et al. |
| 5,320,632 A | 6/1994 | Heidmueller |
| 5,336,239 A | 8/1994 | Gimpelsom |
| 5,339,800 A | 8/1994 | Wiita et al. |
| 5,350,385 A | 9/1994 | Christy |
| 5,354,298 A | 10/1994 | Lee et al. |
| 5,368,601 A | 11/1994 | Sauer et al. |
| 5,374,275 A | 12/1994 | Bradley et al. |
| 5,387,227 A | 2/1995 | Grice |
| 5,391,182 A | 2/1995 | Chin |
| 5,392,766 A | 2/1995 | Masterson et al. |
| 5,403,328 A | 4/1995 | Shallman |
| 5,403,329 A | 4/1995 | Hinchcliffe |
| 5,433,722 A | 7/1995 | Sharpe et al. |
| 5,439,469 A | 8/1995 | Heaven et al. |
| 5,458,609 A | 10/1995 | Gordon et al. |
| 5,462,560 A | 10/1995 | Stevens |
| 5,468,251 A | 11/1995 | Buelna |
| 5,496,335 A | 3/1996 | Thomason et al. |
| 5,499,991 A | 3/1996 | Garman et al. |
| 5,503,634 A | 4/1996 | Christy |
| 5,507,755 A * | 4/1996 | Gresl et al. .................. 606/139 |
| 5,507,757 A | 4/1996 | Sauer et al. |
| 5,562,688 A | 10/1996 | Riza |
| 5,591,180 A * | 1/1997 | Hinchliffe .................... 606/144 |
| 5,626,558 A | 5/1997 | Suson |
| 5,626,614 A | 5/1997 | Hart |
| 5,653,717 A | 8/1997 | Ko et al. |
| 5,817,112 A | 10/1998 | Christoudias |
| 5,953,734 A | 9/1999 | Tanaka |
| 6,066,146 A | 5/2000 | Carroll et al. |
| 6,183,485 B1 | 2/2001 | Thomason et al. |
| 6,258,025 B1 | 7/2001 | Swallert |
| 6,447,444 B1 | 9/2002 | Avni et al. |
| 6,488,691 B1 | 12/2002 | Carroll et al. |
| 6,500,184 B1 | 12/2002 | Chan et al. |
| 6,562,052 B2 * | 5/2003 | Nobles et al. ................. 606/144 |
| 6,709,442 B2 * | 3/2004 | Miller et al. .................. 606/153 |
| 6,755,782 B2 | 6/2004 | Ogawa |
| 6,923,759 B2 | 8/2005 | Kasahara et al. |
| 7,320,693 B2 | 1/2008 | Pollack et al. |
| 8,088,065 B2 | 1/2012 | Karasawa et al. |
| 2002/0049453 A1 * | 4/2002 | Nobles et al. ................. 606/139 |
| 2004/0049207 A1 * | 3/2004 | Goldfarb et al. .............. 606/139 |
| 2004/0087978 A1 | 5/2004 | Velez et al. |
| 2004/0249412 A1 | 12/2004 | Snow et al. |
| 2005/0043746 A1 | 2/2005 | Pollak et al. |
| 2006/0020165 A1 | 1/2006 | Adams |
| 2007/0112425 A1 | 5/2007 | Schaller et al. |

FOREIGN PATENT DOCUMENTS

| | | |
|---|---|---|
| JP | 61069019 | 4/1986 |
| JP | 2005052229 | 3/2005 |
| JP | 2007105314 A | 4/2007 |
| WO | 2009002390 A1 | 12/2008 |

* cited by examiner

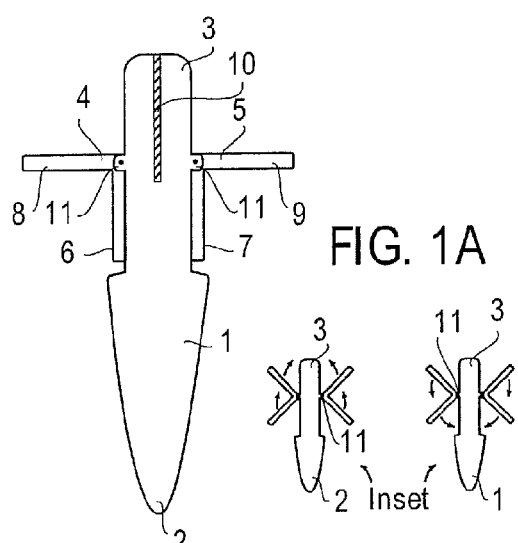
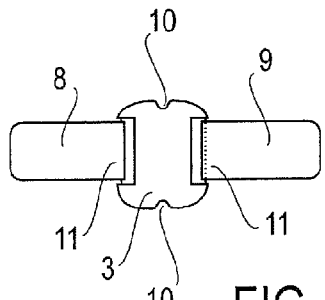
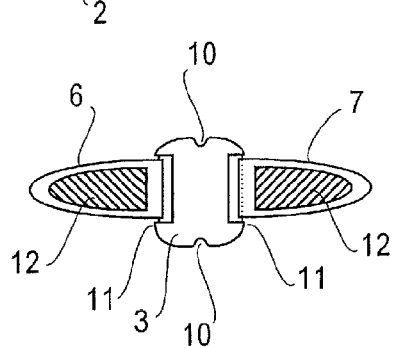
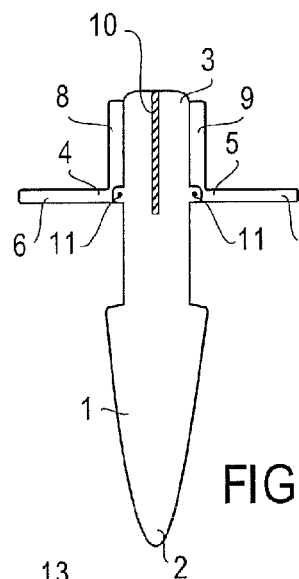
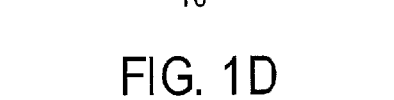
FIG. 1A
FIG. 1B
FIG. 1C
FIG. 1D
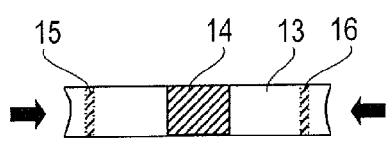
FIG. 2A
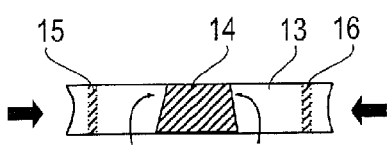
FIG. 2B
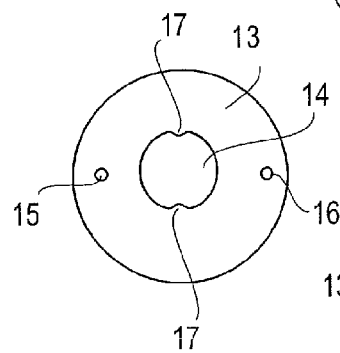
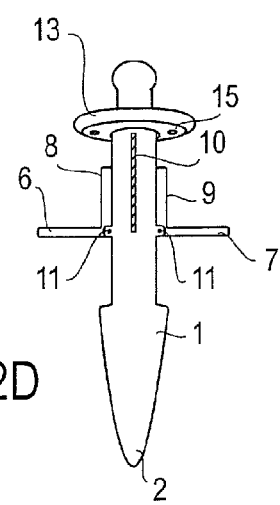
FIG. 2C
FIG. 2D

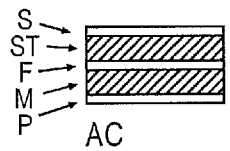
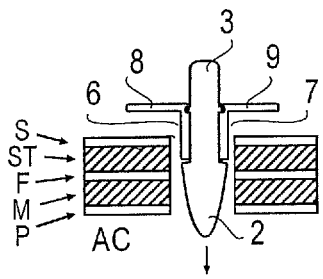
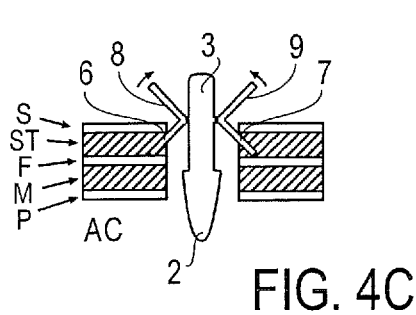
FIG. 4B          FIG. 4C
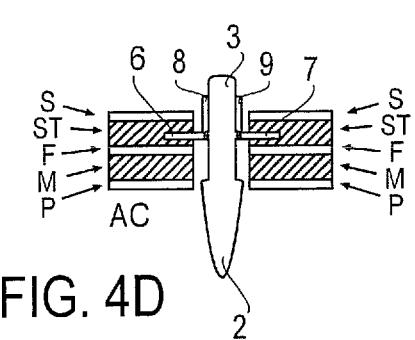
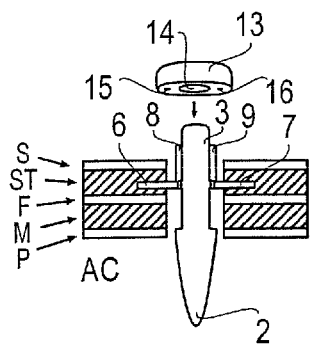
FIG. 4D          FIG. 4E
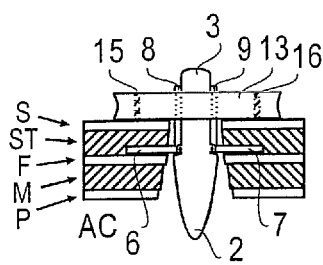
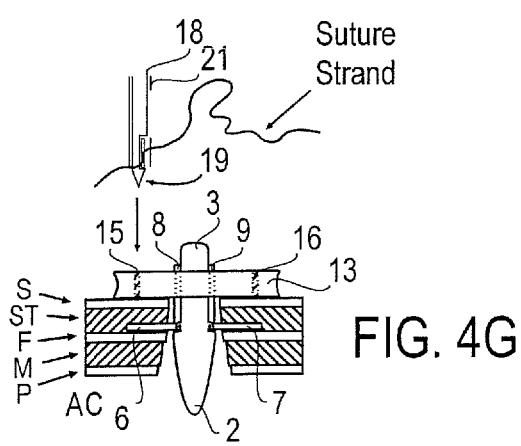
FIG. 4F          FIG. 4G

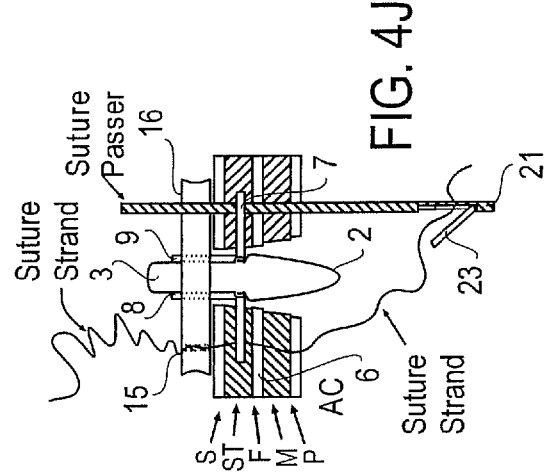
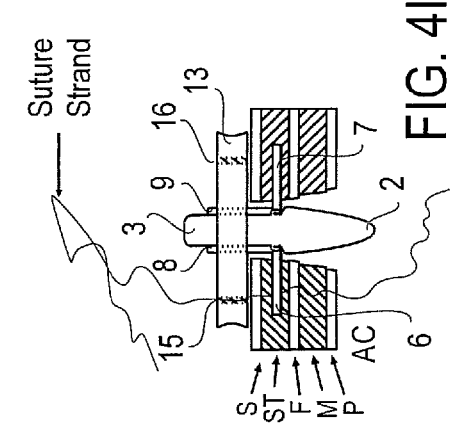
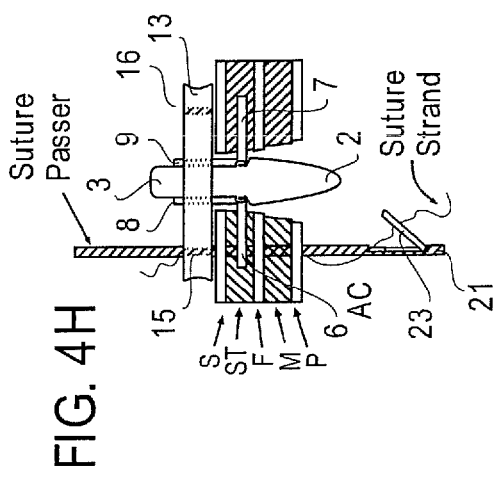
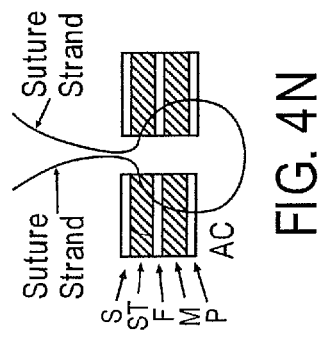
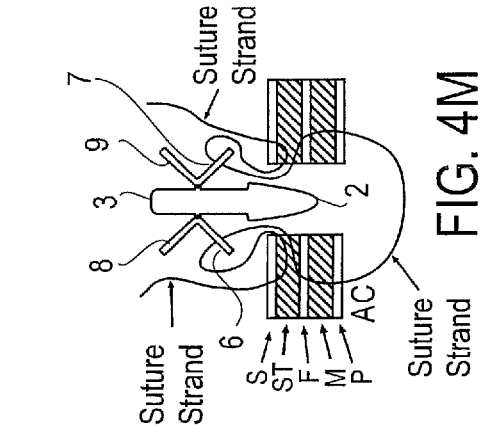
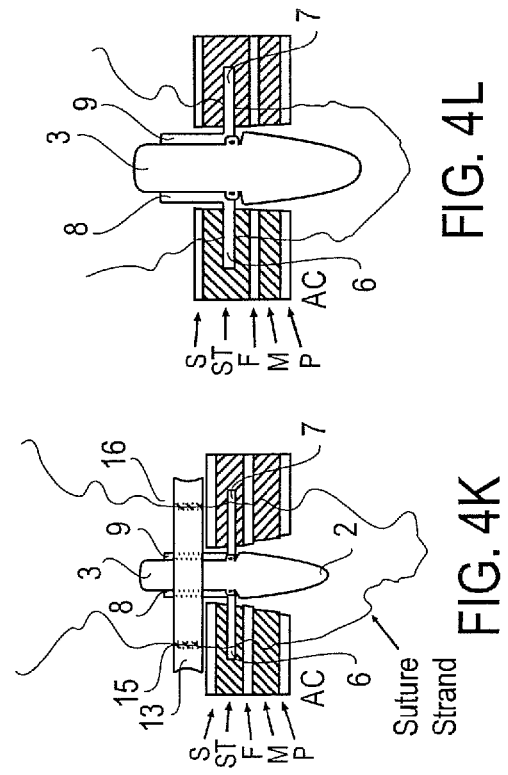

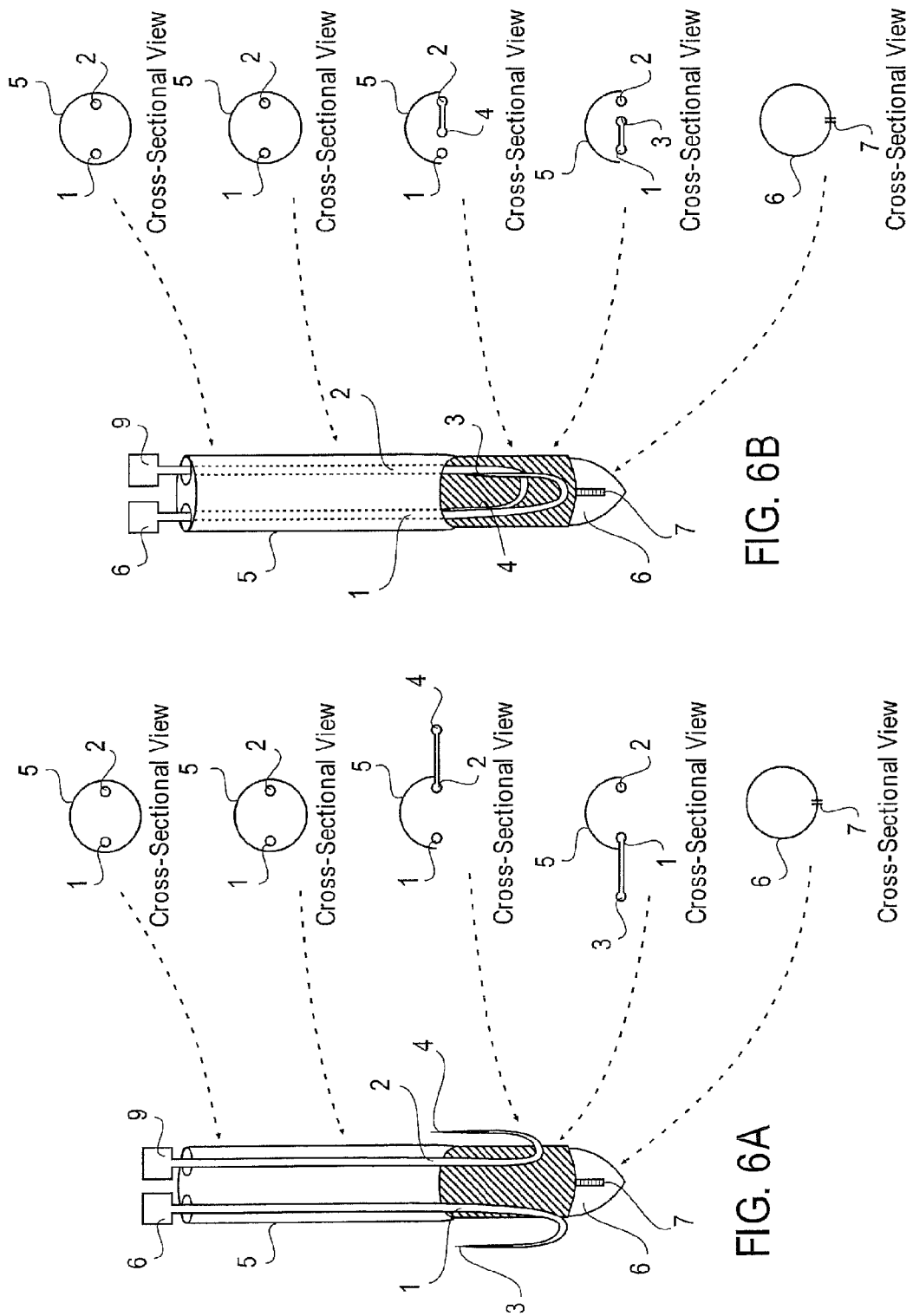

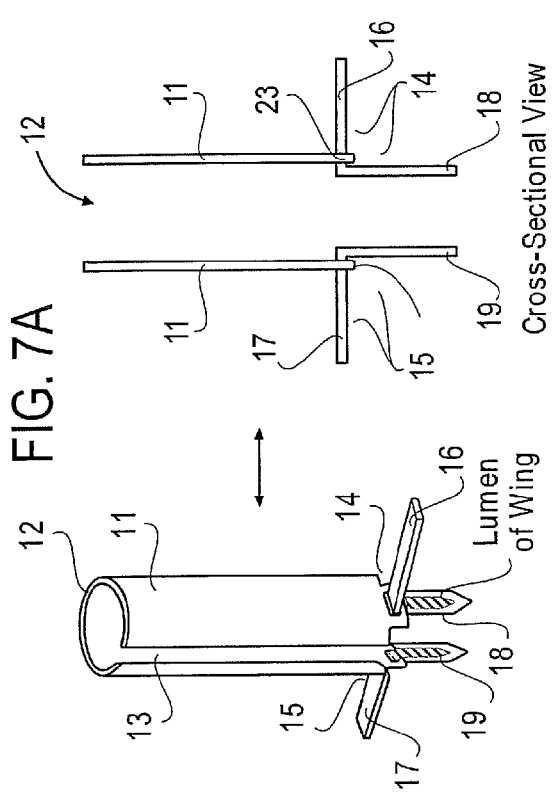
FIG. 7A
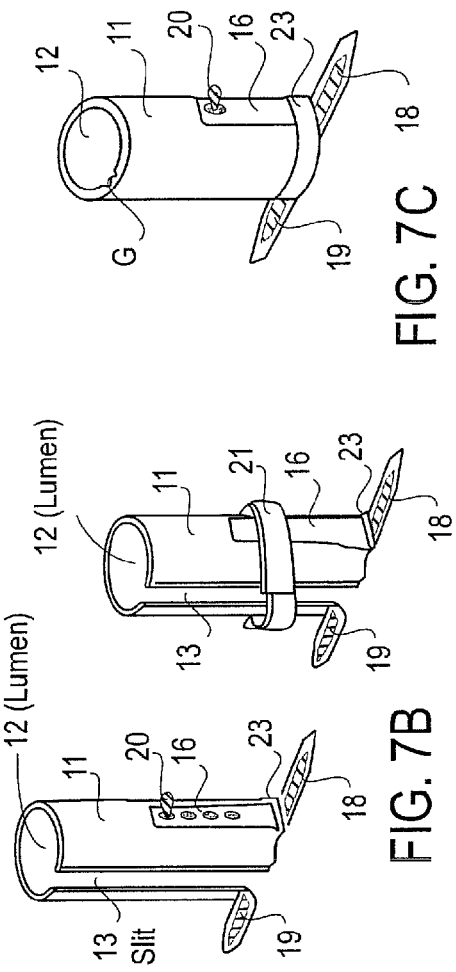
FIG. 7B
FIG. 7C
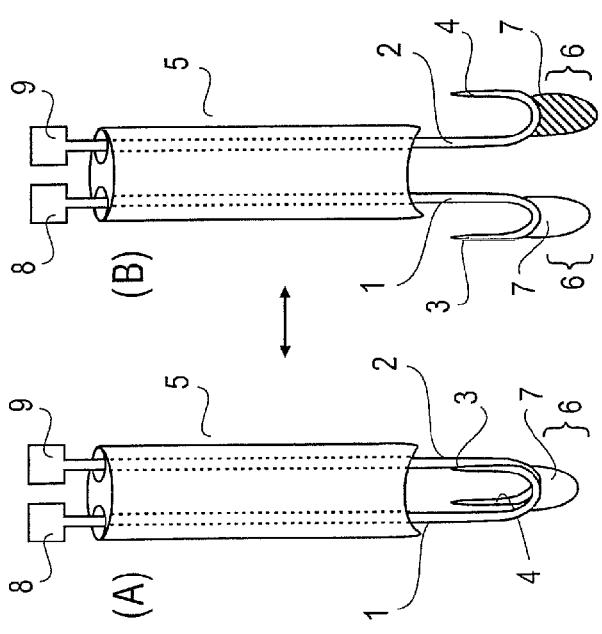
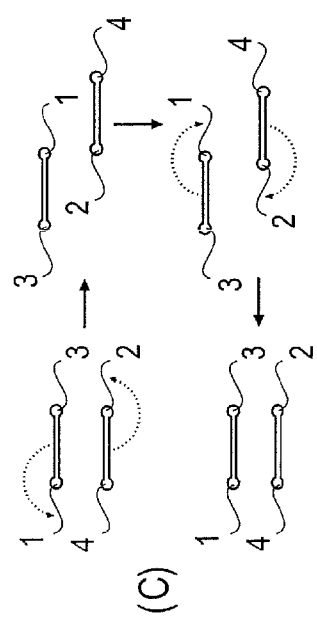
FIG. 6F

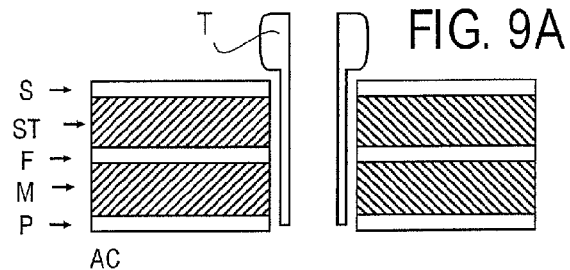
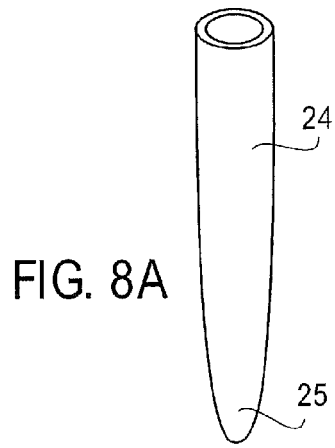
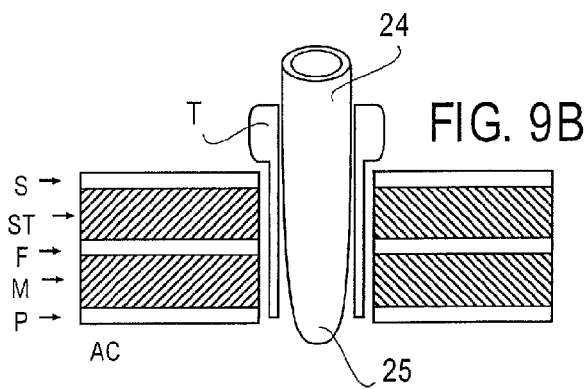
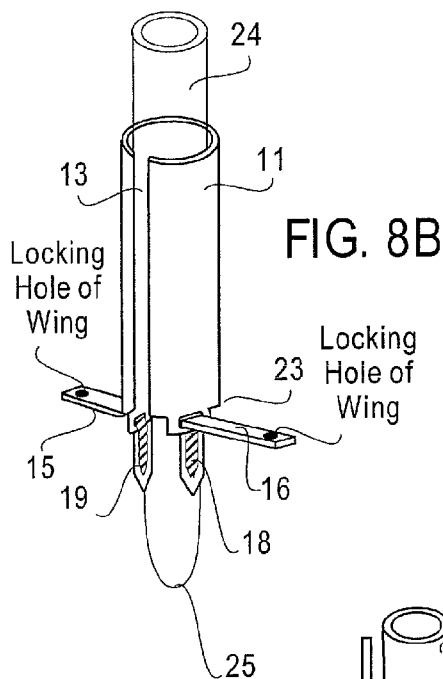
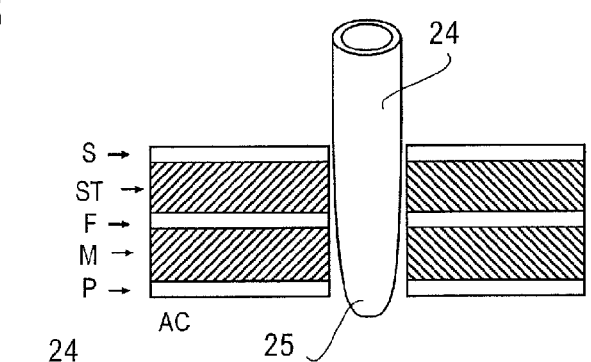
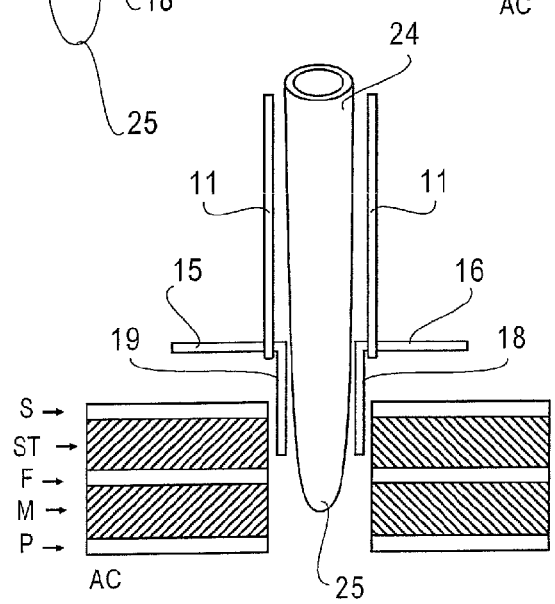

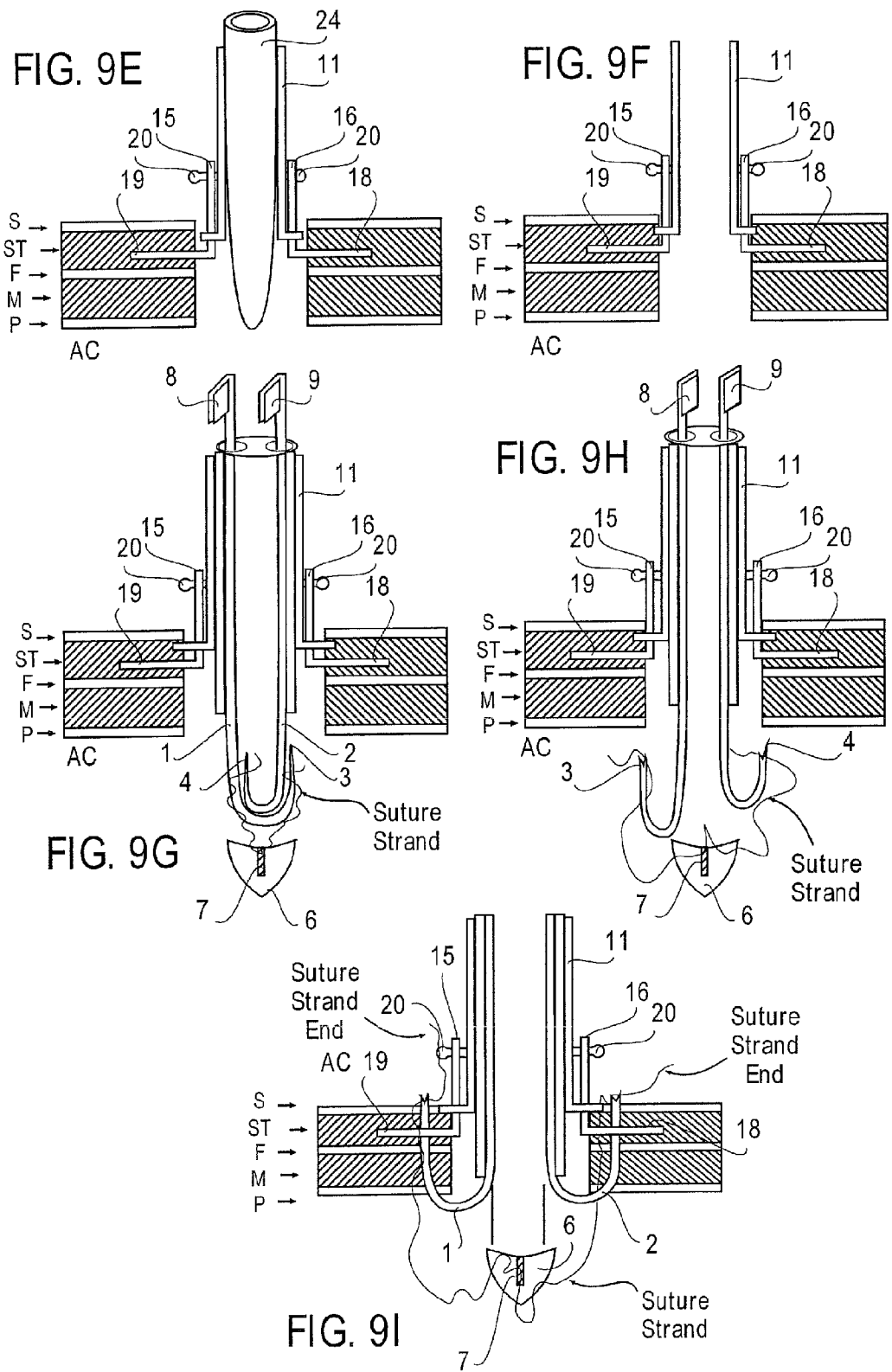

DEVICES AND METHODS FOR CLOSURE OF WOUNDS

FIELD OF THE INVENTION

The invention relates to devices that close the surgical wounds, especially the small wounds from laparoscopic surgery (laparoscopic trocar sites), incorporating various tissue layers except the skin in the closure.

BACKGROUND

Laparoscopic surgery (also known as key-hole surgery or minimally invasive surgery) utilizing small surgical incisions has become a widely popular procedure of choice for many diseases and conditions involving various organ systems in recent years, as it has been shown to provide decreased perioperative patient morbidity. Laparoscopic cholecystectomy (gall bladder removal), appendectomy (appendix removal), hysterectomy (uterus removal), and nephrectomy (kidney removal) are some of the examples. The laparoscopic surgical wounds, although small in size, generally require suture closure to prevent the formation of hernia, in which an intra-abdominal structure such as bowel protrudes through and can be entrapped at the wound site. The incidence of hernia at unclosed laparoscopic wound sites has been reported to be up to 5-6% in the medical literature, and these hernia cases have been often associated with bowel complications requiring reoperation. Even if there is no associated discomfort or bowel entrapment, hernias generally require surgical closure to minimize the risk of potential bowel emergency. Consequently, closure of the laparoscopic trocar wounds, especially those ≥10 mm in size, is generally recommended.

In the closure of the laparoscopic wound sites (from laparoscopic trocar puncture), it is important to close the fascial layer defect, which is located below the skin and subcutaneous fatty layer. The fascia provides most of the strength to the body wall and is the most important layer to close. Peritoneum (the inner most layer of abdominal wall and comes in direct contact with intra-abdominal structures such as bowel) is also important to close as there are reported cases of bowel hernia in obese patients after fascial closure alone. Incorporating the fascial layer and the peritoneal layer in the wound closure constitutes a full-thickness closure, which is the optimal method.

Small surgical wounds from laparoscopic trocar sites are typically closed via open surgical techniques (by directly identifying and hand suturing of the body tissue layers using the conventional open surgical instruments) or via certain medical devices such as Carter-Thomason Suture Passer/CloseSure Device (from Inlet Medical), various double-headed needle-tip suture threading and capture devices, and various single-headed needle-tip suture passing and capture devices (See U.S. Pat. Nos. 5,953,734, 5,496,335, 6,183,485, 7,320,693, 5,562,688, 5,281,234, 5,222,508, 5,503,634, 5,336,239, 5,507,755, 5,320,629, 5,281,237, 5,817,112, 5,499,991, 5,468,251, 5,439,469, 5,350,385, 5,403,328, 5,653,717, 5,387,227, 5,149,329, 5,433,722, 5,462,560, 5,374,275, 5,368,601, 5,320,632, 5,403,329, 5,458,609, 5,626,558, 5,507,757, 5,368,601, 6,500,184, 6,066,146, 5,085,661, 5,626,614, 5,041,129, 5,354,298, 6,488,691, 5,391,182 and published patent application number 20050043746A1, 20040249412A1, 20040087978A1). Open surgical closure is often difficult and time-consuming due to the small size of the incisional opening and the significant depth of the incision. The various medical devices for laparoscopic wound closure listed above were designed to reduce the efforts and closure time needed. Of these, Carter-Thomason system is the most popular. However, full thickness closure (incorporating different body wall layers including the peritoneum and fascial layer except the skin) in a timely manner is often unreliably or inconsistently achieved clinically. In addition, some of the devices may be expensive to manufacture. None of these clinically available devices describe or suggest the present invention. Furthermore, none of the wound closure devices patented previously yet not used clinically describe or suggest the present invention.

There is clearly a long-felt need for devices and methods that provide reliable full-thickness tissue closure at the small surgical wounds such as those in laparoscopic surgery. There is a need for such devices and methods to provide small surgical wound closure in a safe and fast manner. There is a need for such devices that are simple and inexpensive to manufacture, that are simple to use and robust in use, and that can be used with a variety of wound sizes, configurations, and depths. The present invention provides such devices and methods of using them.

Exemplary embodiments of the invention are described in detail by the figures and by the description below.

THE FIGURES

Like all preceding and following discussions, the first variation of the invention will be considered as synonymous with the "outside-in" variation, and the second variation of the invention will be considered as synonymous with the "inside-out" variation.

FIG. 1A illustrates the center piece of the first variation of the device ("outside-in" variation) showing the center piece body (1), its distal end (2) to be inserted into the wound site, its proximal end (3), its 2 ring-like wings (4 and 5), its wing portions with hollow space or lumen (6 and 7), and wing portions without lumen (8 and 9). The wings may be attached to the center piece body via mechanical (such as pivots, rods, joints, rubber or elastic flaps), electrical, electromagnetic, or other means, and a rod/pivot/hinge mechanical attachment mechanism (11) is illustrated in the present embodiment. The wings may move or rotate in relation to the center piece at the attachment site (see the 2 inset figures showing the directions of wing rotation indicated by the arrows). The 2 wings may move or rotate in a manner independent of each other. A rail or groove (10) may be present in some embodiments but absent in certain embodiments. Alternatively, guide or guides based on a protruding design (not shown) may be present in certain embodiments.

FIG. 1B illustrates the top view of the embodiment in FIG. 1A, showing the proximal end of the center piece (3), the wing portions without lumen (8 and 9), and a rod-pivot hinge mechanical joint between each wing and center piece body (11). A rail or groove (10) may be present in certain embodiments but absent in others.

FIG. 1C illustrates the center piece of the first variation of the device ("outside-in" variation) showing the center piece body (1), its distal end (2) to be inserted into the wound site, its proximal end (3), its 2 wings (4 and 5), its wing portions with hollow space or lumen (6 and 7), and wing portions without lumen (8 and 9). The wings may be attached to the center piece body via mechanical (such as pivots, rods, joints, rubber or elastic flaps), electrical, or other means, and a rod/pivot/hinge mechanical attachment mechanism (11) is illustrated in the present embodiment. The wings may move or rotate in relation to the center piece at the attachment site (see the 2 inset figures in FIG. 1A, showing the directions of wing rotation indicated by the arrows). The 2 wings may move or rotate in a manner independent of each other. A rail or groove (10) may be present in some embodiments but absent in certain embodiments. Alternatively, guide or guides based on a protruding design (not shown) may be present in certain embodiments.

FIG. 1D illustrates the top view of the embodiment in FIG. 1C, showing the proximal end of the center piece (3), the wing portions with lumen (6 and 7), a rod-pivot hinge mechanical joint between each wing and center piece body (11), and wing lumen (12). A rail or groove (10) may be present in certain embodiments.

FIG. 2A is a top view of the ring piece of the first variation of the device ("outside-in" variation), with ring body (13), ring lumen or hollow space (14) that accommodates the proximal end of center piece (not shown), and 2 suture passer tunnels (15 and 16). A guide or guides (17), which may be based on a protrusion design into the ring lumen that is accommodated by the groove, slit, or rail of proximal center piece (10 in FIGS. 1A and 1C but not shown in FIG. 2A), may be present in some embodiments. Alternatively, such guide or guides may be absent in certain embodiments. Alternatively, rails, grooves, or other concave design may (not shown) may replace such protruding guide or guides in other embodiments.

FIG. 2B is a cross-sectional side view of the ring piece of the "outside-in" variation of the device, with ring body (13), ring lumen (14), and 2 suture passer tunnels (15 and 16). Indentation on the side wall of the ring piece (indicated by the solid arrows) may be present in certain embodiments to provide ergonomic finger grasping of the ring piece. Note that the suture passer tunnels align with the hollow spaces (lumen) of the wings associated with the center piece (not shown). Such alignment allows direct passage of a suture passer through a suture passer tunnel of the ring piece into the lumen of a wing.

FIG. 2C is a cross-sectional side view of the ring piece of the "outside-in" variation of the device, with ring body (13), ring lumen (14), and 2 suture passer tunnels (15 and 16). Indentation on the side wall of the ring piece (indicated by the solid arrows) may be present in certain embodiments. The top and bottom entrances to the ring lumen (14) may have different dimensions, and the "slanted" configuration of the ring lumen on the cross-sectional side view is indicated by the 2 thin arrows in the figure. Note that the suture passer tunnels align with the hollow spaces (lumen) of the wings associated with the center piece (not shown). Such alignment allows direct passage of a suture passer through a suture passer tunnel of the ring piece into the lumen of a wing.

FIG. 2D is a three-dimensional view of an alternative embodiment of the device. In such embodiment, the ring piece and the center piece of the device may be physically integrated as a single entity as the ring lumen slides along the elongated center piece body yet cannot be detached or removed from the center piece body.

FIG. 3A is a cross-sectional side view of the distal end of the suture passer, with center rod body (18), center rod needle tip (19), center rod concavity (20), outer sheath (21), outer sheath opening (22), jaw (23), and attachment of the jaw to center rod (24). The center rod concavity accommodates the jaw within the outer sheath lumen when the jaw is pushed into a closed position by sliding the outer sheath wall over the jaw. The jaw may be attached to the center rod via mechanical (such as pivots, rods, joints, rubber, elastic flaps . . . etc), electrical, electromagnetic, or other means. Flexible materials with memory such as Nitinol may be used in certain embodiments (see inset picture), in which a bent Nitinol piece replaces the need for a mechanical hinge associated with a spring/rod/pivot mechanism.

FIG. 3B is a cross-sectional side view of the distal end of the suture passer, with center rod body (18), center rod needle tip (19), center rod concavity (20), outer sheath (21), outer sheath opening (22), jaw (23), and attachment of the jaw to center rod (24). The jaw moves or rotates away from the center rod and protrudes through the outer sheath opening (22) by sliding the outer sheath opening over the jaw. In such orientation, the jaw is in the "open" position. The jaw may be attached to the center rod via mechanical (such as pivots, rods, joints, rubber, elastic flaps . . . etc), electrical, electromagnetic, or other means. Flexible materials with intrinsic memory such as Nitinol may be used in certain embodiments (see inset picture), in which a bent Nitinol piece (bent in its resting state) replaces the need for a mechanical hinge associated with a spring/rod/pivot mechanism. Note that the jaw opening points away from the needle tip (19).

FIG. 3C illustrates that a raised edge or protrusion design may be present at the tip of the jaw, to prevent escape of the surgical suture strand captured by the jaw.

FIG. 3D illustrates a different embodiment of the distal end of suture passer, in which the jaw opens to a different direction compared to the embodiments described in FIGS. 3A-3C. Note that the jaw opening points toward the needle tip (19). Center rod body (18), center rod needle tip (19), center rod concavity (20), outer sheath (21), outer sheath opening (22), jaw (23), and attachment of the jaw to center rod (24) are also shown. The jaw may be attached to the center rod via mechanical (such as pivots, rods, joints, rubber, elastic flaps . . . etc), electrical, electromagnetic, or other means. Flexible materials with intrinsic memory such as Nitinol may be used in certain embodiments, in which a bent Nitinol piece replaces the need for a mechanical hinge associated with a spring/rod/pivot mechanism.

FIG. 3E illustrates a variation of the proximal end of suture passer, in which the outer sheath (not shown) movement is controlled by sliding a pad or knob. The control may be achieved via mechanical, electrical, electromagnetic, or other means.

FIG. 3F illustrates a variation of the distal end of suture passer much different from the earlier illustrations (3A-3E), in which the outer sheath is a hollow needle with lumen (25) with a sharp needle-like distal end (26). Along the distal end of the outer sheath shaft (27), there is a slit of various dimension (28) to accommodate the surgical suture (not shown) as the suture is secured to the suture passer. Within the lumen of the outer sheath (25), wire-like jaws (29) with various angulation/curvature design to secure the surgical suture are present. Each jaw may have a hook or protrusion element at its distal tip (30) to facilitate suture capturing. The number of the jaws may vary from 1 to more than 3 to 4. The jaws expand outward away from the axis of the outer sheath as they are advanced beyond the distal tip of outer sheath (26), but they are sufficiently flexible to be retracted within the outer sheath lumen during resting state or during suture capturing state, the latter of which involves suture entrapment with the jaws. The jaws may be made of any material. The deployment mechanism of the jaws (advancement beyond the outer sheath distal end and retraction within the outer sheath lumen) may involve the use of springs and may be based on any mechanical, electrical, or other means.

FIGS. 4A-4N illustrate one possible method of using the invention ("outside-in" variation) to close a trocar wound site.

FIG. 4A is a cross-sectional view of the trocar wound site of the abdominal wall, showing skin (S), subcutaneous tissue layer (ST), external layer of fascia (F) providing strength to body wall, muscle (M), and peritoneum (P). The abdominal cavity space (AC) is below the level of peritoneum (P). These labels apply to the remaining figures under FIG. 4.

FIG. 4B shows the placement of the center piece of the device ("outside-in" variation) into the trocar wound site, with the dark arrow indicating the direction of device insertion towards the abdominal cavity space (AC). Proximal center piece body (3), distal center piece body (2), its 2 wings with portions without lumen (8 and 9), and wings portions with lumen (6 and 7) are shown.

FIG. 4C shows the rotation of the wings at their attachment sites to the center piece body so that the wing portions with lumen (6 and 7) are to be placed within the subcutaneous tissue layer (ST), between the skin (S) and fascia (F). Proximal center piece body (3), distal center piece body (2), its 2 wings with portions without lumen (8 and 9), and wings portions with lumen (6 and 7) are shown. The direction of rotation of the wings in relation to the center piece is indicated by the dark solid arrows.

FIG. 4D shows the center piece of the device with its wings (portions with lumen—6 and 7) positioned within the subcutaneous tissue layer (ST). Proximal center piece body (3), distal center piece body (2), its 2 wings with portions without lumen (8 and 9), and wings portions with lumen (6 and 7) are shown.

FIG. 4E shows the attachment of the ring piece body (13) of the device to the proximal center piece (3) with the wing portions without lumen (8 and 9). The ring lumen (4) accommodates both the proximal center piece (3) and the wing portions without lumen (8 and 9). The ring lumen (14) may fit or engage the proximal center piece (3) and its wing portions without lumen (8 and 9) via a design involving grooves/slits/rails (such as 10 in FIG. 1A and 17 in FIG. 2A), which is not shown in the present figure, and such design is intended to prevent rotation of the ring piece in relation to the center piece. Proximal center piece body (3), distal center piece body (2), its 2 wings with portions without lumen (8 and 9), wings portions with lumen (6 and 7), and suture passer tunnels of the ring piece (15 and 16) are shown.

FIG. 4F shows the completion of the attachment of the ring piece body (13) of the device to the proximal center piece (3) with the wing portions without lumen (8 and 9). The ring lumen (not labeled) now accommodates both the proximal center piece (3) and the wing portions without lumen (8 and 9). The ring lumen may fit or engage the proximal center piece (3) and its wing portions without lumen (8 and 9) via various designs such as that involving grooves/slits/rails (such as 10 in FIG. 1A and 17 in FIG. 2A), which is not shown in the present figure, and such design is intended to prevent rotation of the ring piece in relation to the center piece. Proximal center piece body (3), distal center piece body (2), its 2 wings with portions without lumen (8 and 9), wings portions with lumen (6 and 7), and suture passer tunnels (15 and 16) of the ring piece are shown.

FIG. 4G shows the insertion of the suture passer with a suture strand secured to its distal tip (as the suture strand is entrapped by the closed jaw of the suture passer) into one of the 2 suture passer tunnels of the ring piece of the device (15 in the present figure). Proximal center piece body (3), distal center piece body (2), its 2 wings with portions without lumen (8 and 9), wings portions with lumen (6 and 7), ring piece body (13), suture passer tunnels (15 and 16) of the ring piece, needle tip of suture passer (19), center rod of suture passer (18), outer sheath of suture passer (21), and jaw of suture passer (23) are shown.

FIG. 4H shows the suture strand is being released into the abdominal cavity space from the suture passer distal tip by sliding the outer sheath over the jaw, thereby opening the jaw. Proximal center piece body (3), distal center piece body (2), its 2 wings with portions without lumen (8 and 9), wings portions with lumen (6 and 7), ring piece body (13), suture passer tunnels (15 and 16) of the ring piece, outer sheath of suture passer (21), and jaw of suture passer (23) are shown. Note that in certain embodiments, the outer sheath (21) protrudes beyond the limit of the needle tip of the suture passer (not shown) as the jaw (23) is open, thereby preventing injury to the intra-abdominal organs or structures from the sharp needle tip. Note that the suture passer penetrates through all layers of the body wall (from skin to peritoneum) as well as the lumen of one wing of the device (6).

FIG. 4I shows that one end of the suture strand has been left inside the abdominal cavity space (AC) after the removal of the suture passer from the surgical site. Proximal center piece body (3), distal center piece body (2), its 2 wings with portions without lumen (8 and 9), wings portions with lumen (6 and 7), ring piece body (13), and suture passer tunnels (15 and 16) of the ring piece are shown. Note that the suture strand travels through all the layers of the abdominal wall, from skin (S) to peritoneum (P).

FIG. 4J shows that the suture passer jaw is open and ready to secure the suture strand end inside the abdominal cavity, after its insertion through the second suture passer tunnel of the ring piece (16), all tissue layers of the abdominal wall (from skin to peritoneum), as well as the wing portion with lumen of the device (7). Proximal center piece body (3), distal center piece body (2), its 2 wings with portions without lumen (8 and 9), wings portions with lumen (6 and 7), ring piece body (13), suture passer tunnels (15 and 16) of the ring piece, outer sheath of suture passer (21), and jaw of suture passer (23) are shown. Note that in certain embodiments, the outer sheath (21) protrudes beyond the limit of the needle tip of the suture passer (not shown) as the jaw (23) is open, thereby preventing injury to the intra-abdominal organs or structures from the sharp needle tip.

FIG. 4K shows the suture strand path at the wound site following the removal of the suture passer (not shown), which is used to capture the intra-abdominal suture suture strand end in FIG. 4J and pull the strand end out of the abdominal cavity to the space outside the skin. Proximal center piece body (3), distal center piece body (2), its 2 wings with portions without lumen (8 and 9), wings portions with lumen (6 and 7), ring piece body (13), suture passer tunnels (15 and 16) of the ring piece are shown. Note that the suture travels through one suture passer tunnel of the ring piece (15) and all layers of the abdominal wall (from skin to peritoneum), enters the abdominal cavity space, exits the abdominal cavity space, travels through all layers of the abdominal wall and the second suture passer tunnel of the ring piece (16), and returns to the space outside the skin.

FIG. 4L shows the device and suture assembly at the wound site after the removal of the ring piece (not shown). Proximal center piece body (3), distal center piece body (2), its 2 wings with portions without lumen (8 and 9), wings portions with lumen (6 and 7) are shown. Note that the suture travels through all layers of the abdominal wall (from skin to peritoneum), enters the abdominal cavity space, exits the abdominal cavity space, travels through all layers of the abdominal wall, and returns to the space outside the skin.

FIG. 4M shows the removal of the center piece of the device away from the wound site while the suture strand is being left behind. Proximal center piece body (3), distal center piece body (2), its 2 wings with portions without lumen (8 and 9), wings portions with lumen (6 and 7) are shown. Note that the suture travels through all layers of the abdominal wall (from skin to peritoneum), enters the abdominal cavity space, exits the abdominal cavity space, travels through all layers of the abdominal wall, and returns to the space outside the skin. Also note the suture strand portions outside the skin are pulled into the subcutaneous tissue (ST) and the lumen of the wound site during the center piece removal.

FIG. 4N shows the path of the single suture strand at the wound site after the removal of the device. Note that the suture travels through all layers of the abdominal wall below the skin level (including fascia and peritoneum), enters the abdominal cavity space, exits the abdominal cavity space, and travels through all layers of the abdominal wall below the skin level (including peritoneum and fascia). The 2 ends of the suture strand can then be tied to each other for wound closure. Note that skin is not incorporated into the wound closure.

FIG. 4O illustrates one variation of the present device, in which the proximal end of center piece (3), distal end of center piece (2), wings with lumen (6 and 7), wings without lumen (8 and 9), ring piece body (13) with suture passer tunnels (15 and 16) are shown. In this variation, the center piece has a lumen that accommodates a tubular rod with a proximal end (31) and a distal end that is composed of 2 wings (32 and 33). In diagram (A), the distal end of the central tubular rod is retracted within the lumen of distal center piece (2), thereby allowing the 2 wings (32 and 33) of the distal end of the central tubular rod to be brought in proximity to each other and to provide a smooth, tapered contour to the distal end of the device. In diagram (B), the distal end of the central tubular rod is pushed (distally) out of the distal center piece (2) lumen, thereby allowing the 2 wings (32 and 33) of the distal end of the central tubular rod to be separated from each other. In diagram (B), the 2 wings (32 and 33) are connected to the distal end of central tubular rod (35) via a connection mechanism (34), which may be of any mechanical, electromagnetic, or any other means or design. Use of spring may be involved in such mechanism (34). Diagram (C) illustrates various types of possible mechanical design of the connection (34), which is located between the distal end of central tubular rod (35) and the 2 wings (32 and 33). Please note that the angle (Z) between the 2 wings in separated position may be variable, from 1 degree to 359 degrees, but it is designed preferably in the range of 90 to 180 degrees. Diagram (D) illustrates the 3-dimensional view of the 2 wings (32 and 33) of the distal central tubular rod. In one variation of such wings, each wing has a slit that can capture/secure one terminal end of the suture strand. In one variation, each wing may be hollow (shell-like), in which the body of the suture strand can be stored or housed. In another variation, each wing may be solid, and the contact surface of the 2 wings may be flat or grooved. It should be noted that the suture strand terminal ends may be reversibly attached to/captured by the wings (32 and 33) via any type of design or means, including slits, clips, jaw . . . etc.

FIG. 4P illustrates the different types of possible deployment of the specific variations (of the present device) described in FIG. 4O. One possible deployment method is shown in diagram (A), in which the 2 wings (32 and 33) of the distal end of tubular rod are secured to and carry the 2 terminal ends of the suture strand through the wound into the body cavity. The mid-portion of the suture strand is outside the wound (that is, not within the abdominal cavity). Note that distal center piece (2), proximal center piece (3), ring piece (13) with its 2 suture passer tunnels (15 and 16), wings without lumen (8 and 9), wings with lumen (6 and 7), distal end of tubular rod (35) that is well retracted within lumen of center piece are shown. Again, skin (S), subcutaneous tissues (ST), fascia (F), muscle (M), peritoneum (P), and abdominal cavity (AC) are shown. Another possible deployment method is shown in diagram (B1), in which the 2 wings (32 and 33) of the distal end of the tubular rod are secured to and carry the 2 terminal ends of the suture strand into the body cavity. The body (including mid-portion) of the suture strand is stored/housed within the hollow cavity of the wings (32 and 33), as described in FIG. 4O diagram (D). When the distal tubular rod is pushed distally, as in diagram (B2), the 2 wings (32 and 33) become separated from each other, allowing the suture strand body to be dropped into/placed within abdominal cavity, while the terminal ends of the suture strand remain secured to the 2 wings (32 and 33).

FIGS. 4Q-X illustrate one possible method of using the invention ("outside-in" variation) to close a trocar wound site. The specific variation of the invention described in FIG. 4O and FIG. 4P(A) is illustrated.

FIG. 4Q shows the same cross-sectional view of the trocar wound site of the abdominal wall, showing skin (S), subcutaneous tissue layer (ST), external layer of fascia (F) providing strength to body wall, muscle (M), and peritoneum (P). The abdominal cavity space (AC) is below the level of peritoneum (P). The different components of the invention, including distal center piece (2), proximal center piece (3), wings without lumen (8 and 9), wings with lumen (6 and 7), ring body (13) with its suture passer tunnels (15 and 16), proximal central tubular rod (31), and the 2 distal wings of the central tubular rod (32 and 33) in retracted position/partially positioned within lumen of distal center piece (2) are shown. These labels apply to the remaining FIGS. 4Q-X). Note that the wings with lumen (6 and 7) have been positioned within the subcutaneous tissue layer (ST). Note that the ring piece (13) has locked the wings without lumen (8 and 9) in place so that the wings with lumen (6 and 7) are anchored within the ST layer without movement. Note that the 2 terminal ends of the suture strand are secured to the 2 distal wings of the central tubular rod (32 and 33) while the body/mid-portion of the suture strand is outside the abdominal cavity (AC).

FIG. 4R illustrates the separation of the 2 distal wings of the central tubular rod (32 and 33) by pushing the proximal central tubular rod (31) distally towards the abdominal cavity. Note that the 2 terminal ends of the suture strand remain secured to the 2 distal wings of the central tubular rod (32 and 33).

FIG. 4S illustrates the placement of the suture needle passer through one of the suture passer tunnels of the ring piece (15), full thickness abdominal wall (layers S, ST, F, M, P) into abdominal cavity (AC) to capture the first terminal end of the suture strand. One variation of the suture passer described previously (FIG. 3F) is shown, with its wire-like jaws (29) protruding from its distal sheath with sharp end (26). The jaws (29) of suture passer are used to capture the first terminal end of suture strand and detach it from the distal wing of central tubular rod (32).

FIG. 4T illustrates that the first terminal end of the suture has been brought through the full-thickness abdominal wall and the suture passer tunnel of ring piece (15). This is achieved by withdrawing the suture passer proximally away from the abdominal cavity (AC) with the captured first terminal end of suture strand. The first terminal end of suture strand is now outside the abdominal cavity (AC).

FIG. 4U illustrates the placement of the suture needle passer through the opposite suture passer tunnel of the ring piece (16), full thickness abdominal wall (layers S, ST, F, M, P) into abdominal cavity (AC) to capture the second terminal end of the suture strand. One variation of the suture passer described previously (FIG. 3F) is shown, with its wire-like jaws (29) protruding from its distal sheath with sharp end (26). The jaws (29) of suture passer are used to capture the second terminal end of suture strand and detach it from the distal wing of central tubular rod (33).

FIG. 4V illustrates that the second terminal end of the suture has been brought through the full-thickness abdominal wall and the suture passer tunnel of ring piece (16). This is achieved by withdrawing the suture passer proximally away from the abdominal cavity (AC) with the captured second terminal end of suture strand. The second terminal end of suture strand is outside the abdominal cavity (AC). Note that the suture travels through one suture passer tunnel of the ring piece (15) and all layers of the abdominal wall (from skin to peritoneum), enters the abdominal cavity space, exits the abdominal cavity space, travels through all layers of the abdominal wall and the second suture passer tunnel of the ring piece (16), and returns to the space outside the skin.

FIG. 4W illustrates the removal of the invention from the wound site while the suture strand is being left behind. Note that the suture travels through all layers of the abdominal wall (from skin to peritoneum), enters the abdominal cavity space, exits the abdominal cavity space, travels through all layers of the abdominal wall, and returns to the space outside the skin. Also note the suture strand portions outside the skin are pulled into the subcutaneous tissue (ST) and the lumen of the wound site during the removal of the invention.

FIG. 4X shows the path of the single suture strand at the wound site after the removal of the device. Note that the suture travels through all layers of the abdominal wall below the skin level (including fascia and peritoneum), enters the abdominal cavity space, exits the abdominal cavity space, and travels through all layers of the abdominal wall below the skin level (including peritoneum and fascia). The 2 ends of the suture strand can then be tied to each other for wound closure. Note that skin is not incorporated into the wound closure.

FIG. 5 (5A-K) illustrates another embodiment of the first variation of the invention ("outside-in" variation).

FIG. 5A illustrates the rod portion of the device, with its distal end associated with a wing with hollow space (lumen). The wing may be of any dimension, material, configuration, or design. The rod may be made from any material, dimension, or design.

FIG. 5B shows that the hollow wing of the distal rod is inserted into the subcutaneous tissue (ST) at the trocar wound site. Skin (S), subcutaneous tissue (ST), fascia (F), muscle (M), peritoneum (P), and abdominal cavity space (AC) are also shown. These labels apply to the remaining figures under FIG. 5.

Figure 3A:
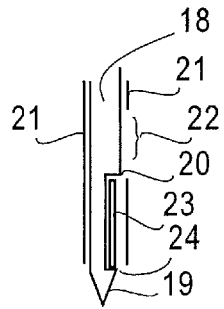
Figure 3B:
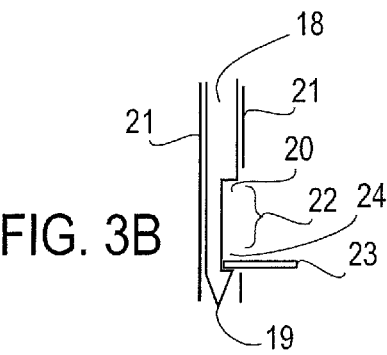
Figure 3C:
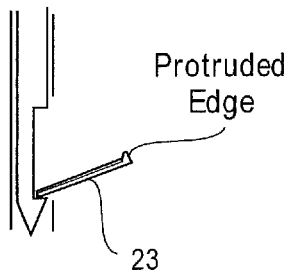
Figure 3D:
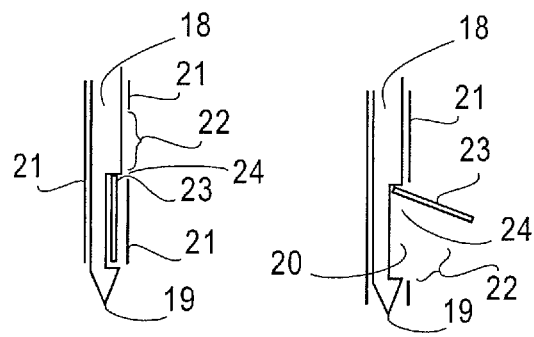
Figure 3E:
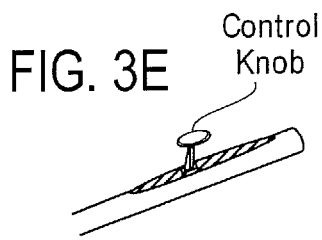
Figure 3F:
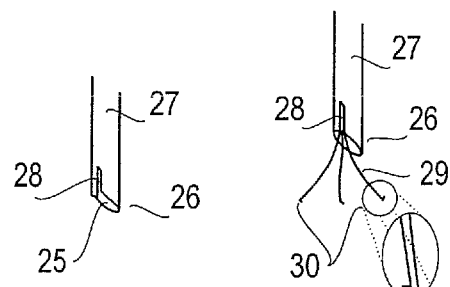
Figure 4O:
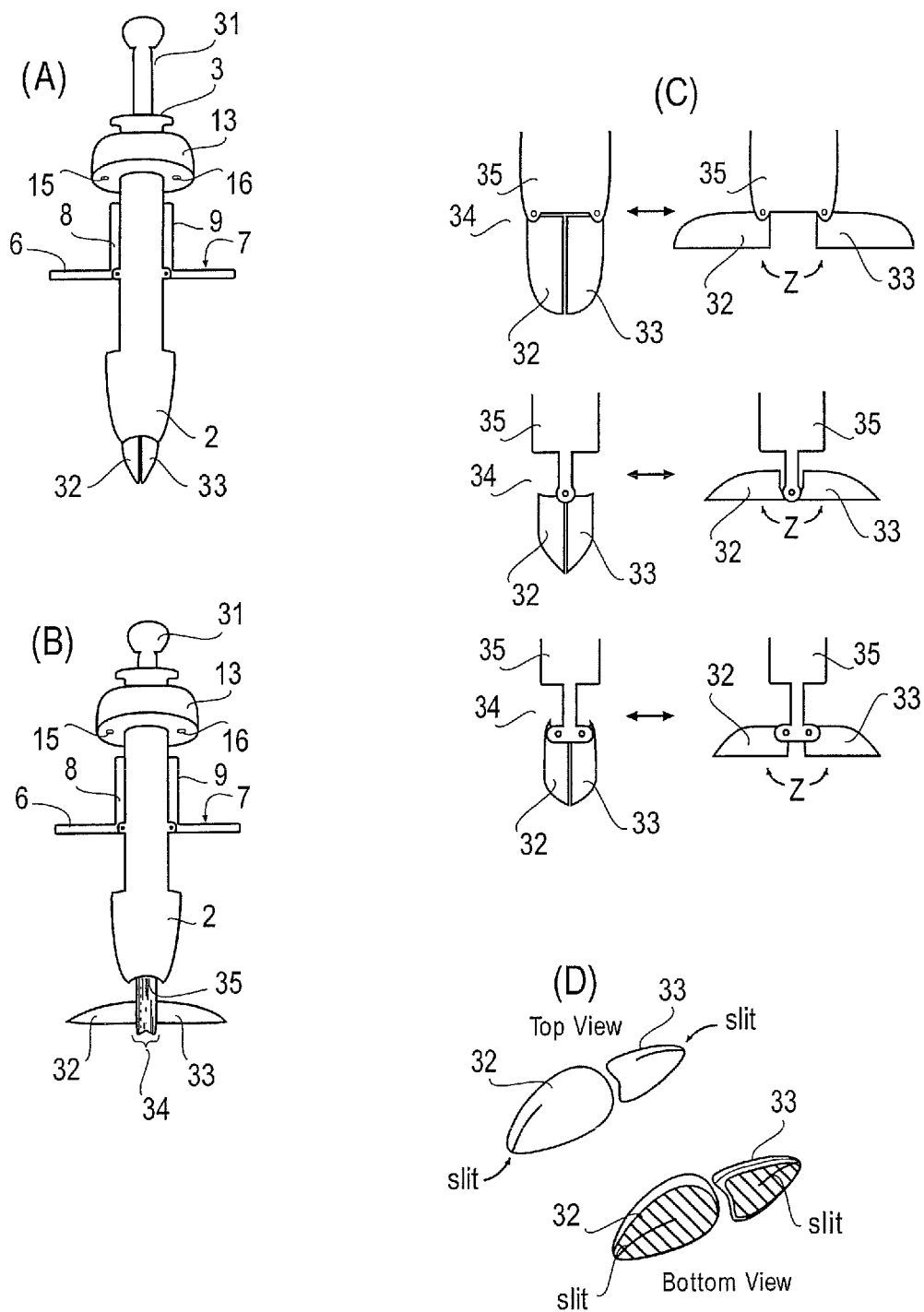
Figure 4P:
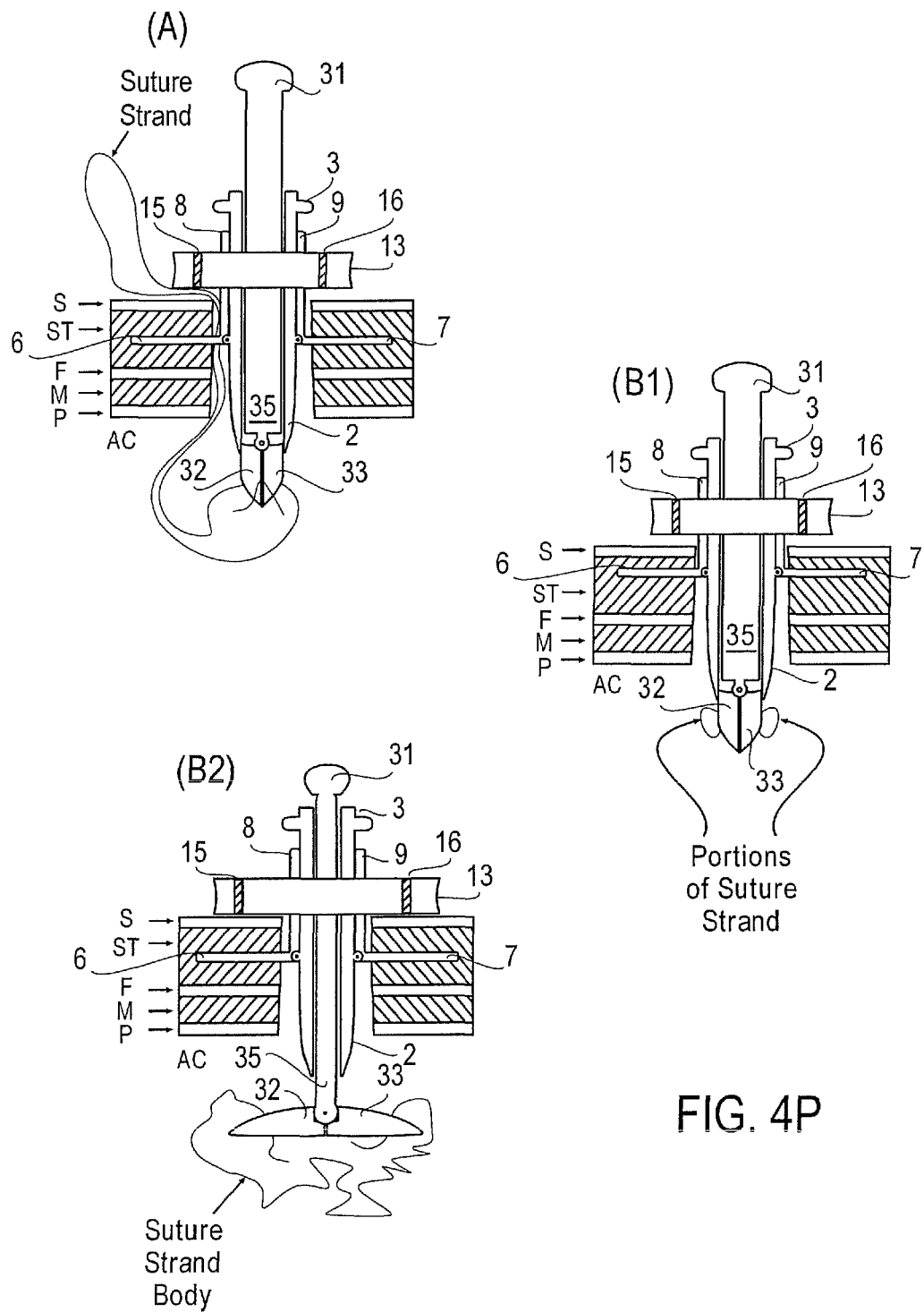
Figure 4Q:
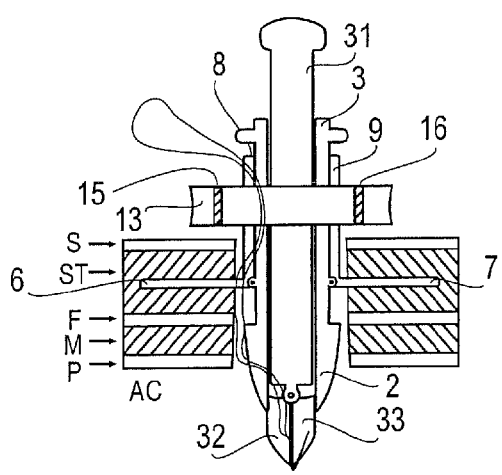
Figure 4R:
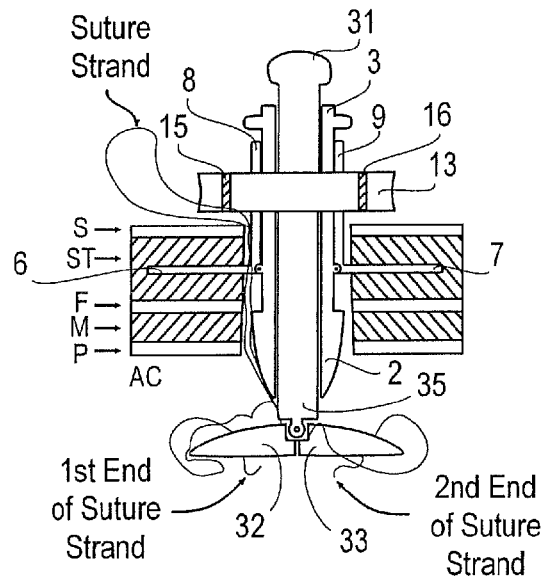
Figure 4S:
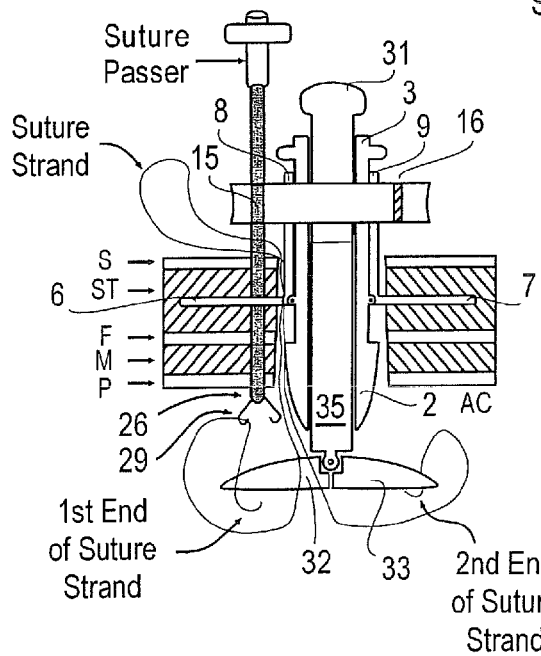
Figure 4T:
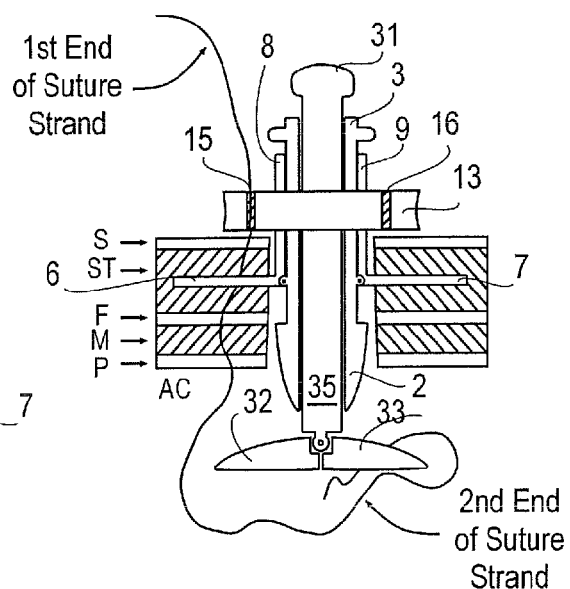
Figure 4U:
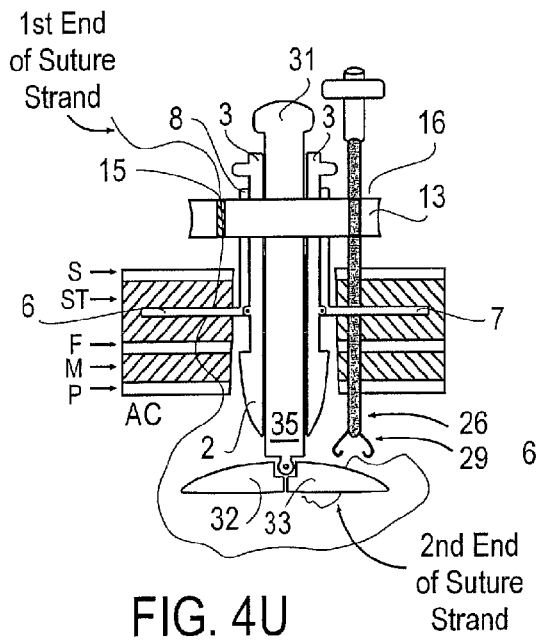
Figure 4V:
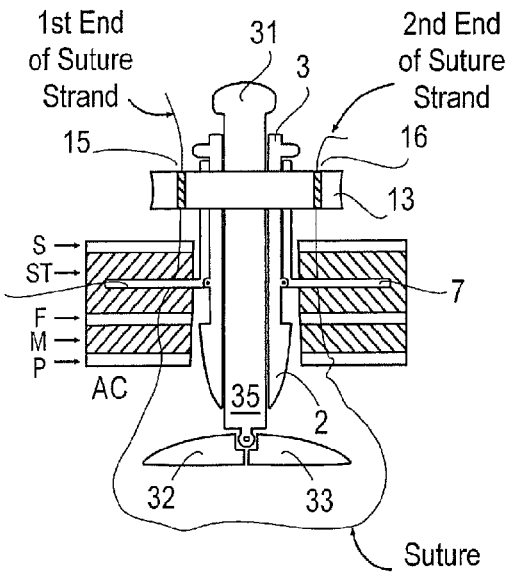
Figure 4W:
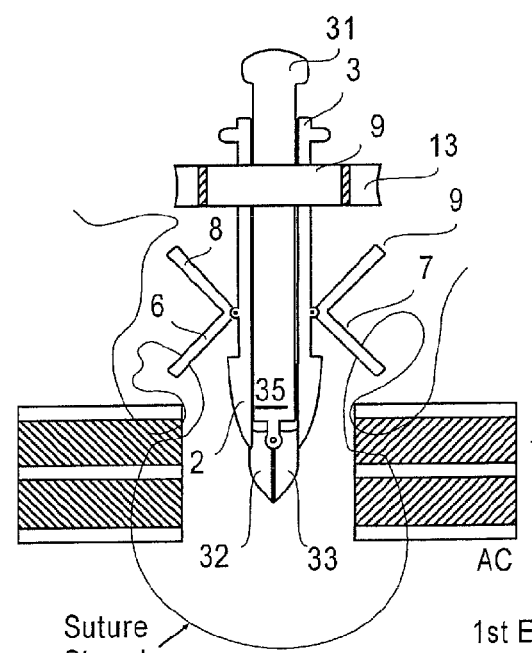
Figure 4X:
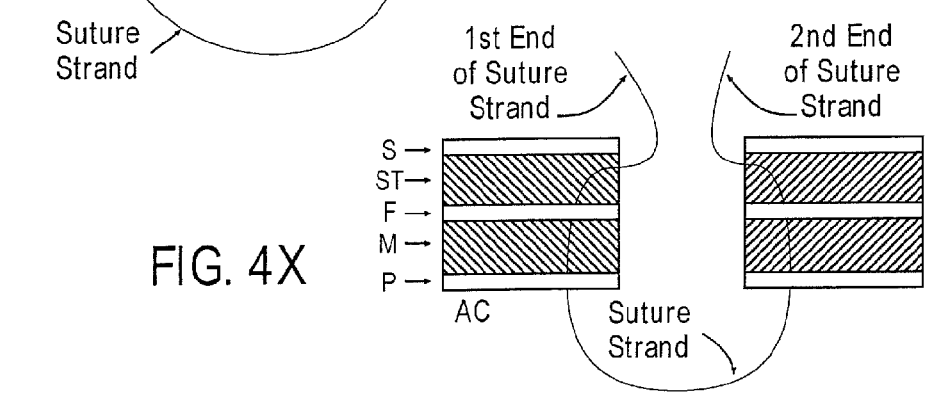
Figure 5A:
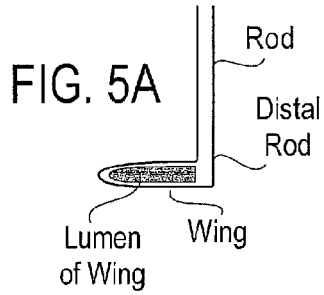
FIG. 5C shows that a suture passer with its distal end secured to a suture strand has been inserted through all tissue layers of the abdominal wall (from skin to peritoneum) into the abdominal cavity space (AC). The suture passer may or may not be identical to that described in FIG. 3A-E.
FIG. 5D shows that after the removal of the suture passer, the suture travels through the skin, subcutaneous tissue, lumen of the wing at distal end of the rod, fascia, muscle, and peritoneum into the abdominal cavity space.
FIG. 5E shows that the suture strand portion outside the skin is pulled into the subcutaneous tissue layer and lumen of the wound while the wing of the distal rod is being removed from the wound site.
FIG. 5F shows that the suture travels from outside the skin, through all layers of body wall (except skin), and into the abdominal cavity space. The rod device with hollow wing has been removed.
FIG. 5G shows that the hollow wing of the rod of the device is placed into the subcutaneous tissue layer on the opposite side of the wound lumen.
Figure 5B:
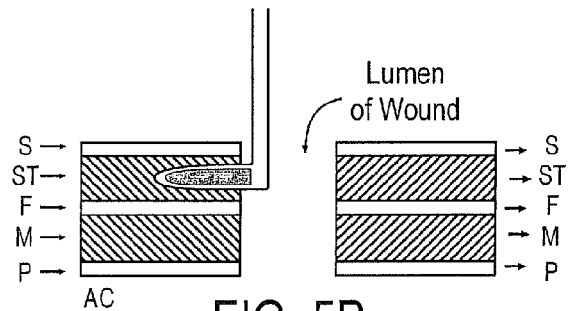
Figure 5C:
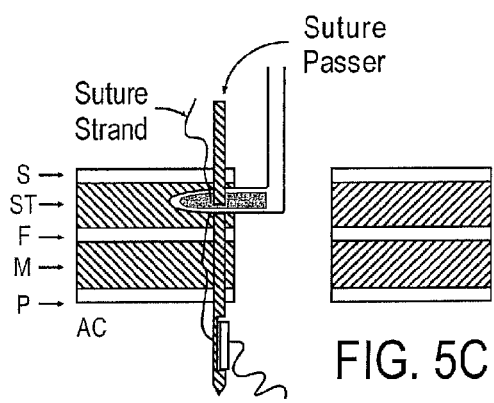
Figure 5D:
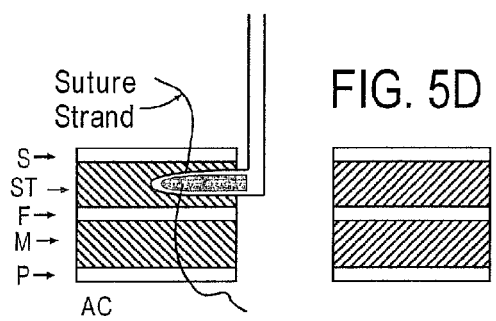
Figure 5E:
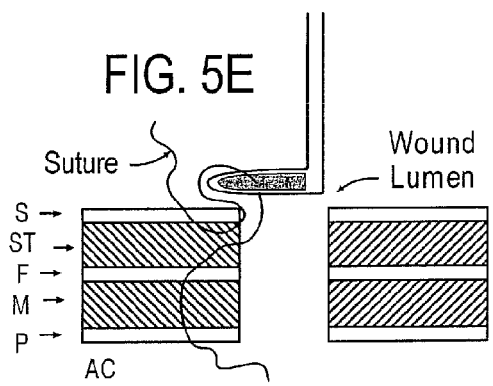
Figure 5F:
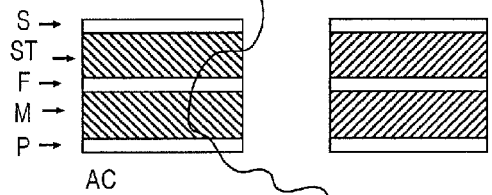
Figure 5G:
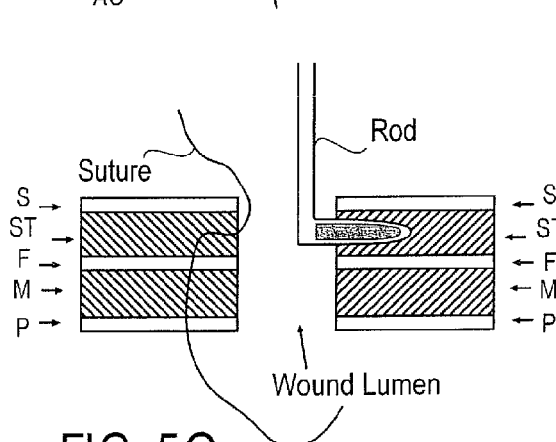
Figure 5H:
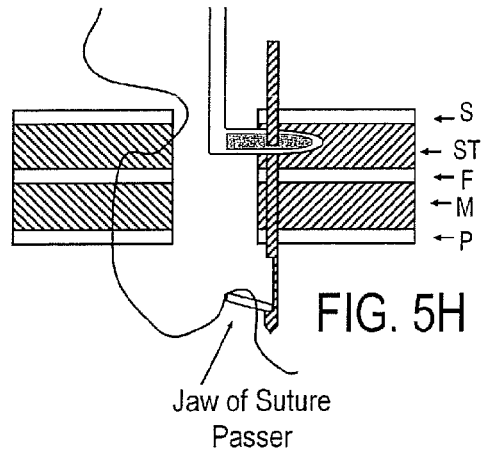

FIG. 5H shows that the suture passer has been placed through all abdominal wall layers (from skin to peritoneum), through the wing lumen of the distal rod, and into the abdominal cavity space. The suture passer is then used to secure the end of the suture strand previously left inside the abdominal cavity. The jaw of the suture passer is shown to be open, ready to entrap the suture end.

Figure 5I:
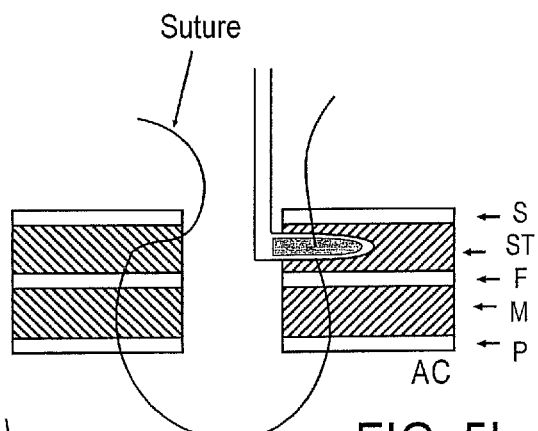

FIG. 5I shows that the suture travels through the subcutaneous tissue layer/fascia/muscle/peritoneum, enters abdominal cavity space, exits abdominal cavity space, travels through all body wall layers (peritoneum/muscle/fascia/subcutaneous tissue/skin), and exits into the space outside the skin. Note that the suture also travels through the lumen of the wing of the device.

Figure 5J:
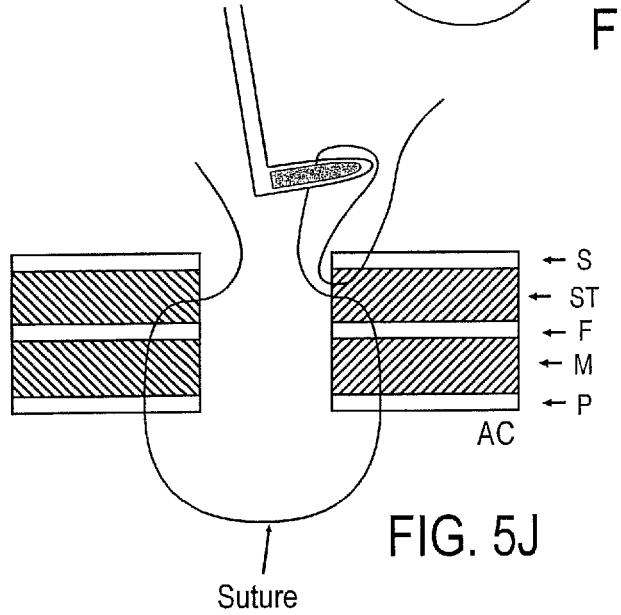

FIG. 5J shows that suture strand portion outside the skin is pulled into the subcutaneous tissue layer and the wound lumen while the wing of the distal rod is being removed from the wound site.

Figure 5K:
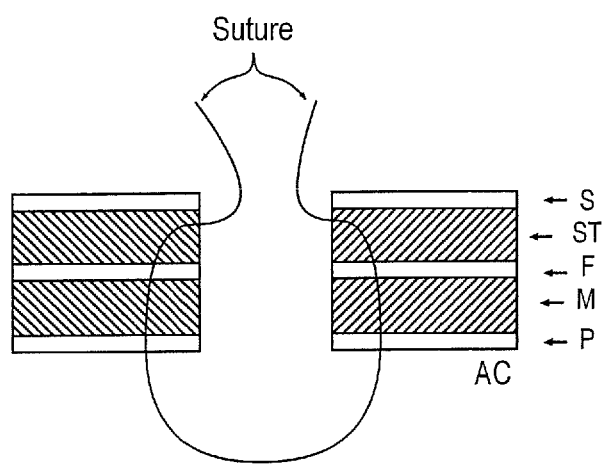

FIG. 5K shows the path of the suture strand: it travels from outside the skin, through wound lumen, through subcutaneous tissue/fascia/muscle/peritoneum, into abdominal cavity, through peritoneum/muscle/fascia/subcutaneous tissue, into wound lumen, and into space outside the skin. The 2 ends of the suture can then be tied to each other to provide wound closure without incorporating the skin.

FIG. 6A illustrates the center piece of the second variation of the invention (the "inside-out" variation). It consists of a pair of J-shaped or U-shaped (inverted) hooks (1 and 2) whose sharp distal ends (3 and 4) can be attached to the ends of a suture strand. The shafts of the 2 hooks (1 and 2) may be accommodated within the lumen of a elongated shell (5). (Note that the shell may be absent in certain embodiments.) The shell may have a tapered distal end (6), which may have a slit or other types of suture strand carrying mechanism (7). The suture strand carrying mechanism may be a simple slit at one side of the distal shell wall (shown in the present figure), clip, hole, spring-loaded grasper, . . . etc, encompassing any type of mechanical, electromagnetic, electrical, or other means and any type of dimension and design. This suture carrying mechanism may be located at any part of the center piece of the device. Rotation (clockwise or counter clockwise) of the proximal ends of the hooks (8 and 9), associated with the proximal end of the shell in the present embodiment, leads to the rotational movements of the hooks (that is, rotation along their respective longitudinal axis—therefore, the distal ends of the hooks may be positioned inside or outside the shell lumen by rotating their respective proximal ends). In FIG. 6A, the distal needle ends of the hooks (3 and 4) are rotated outward and 180 degrees away from each other and, therefore, are outside the shell (5). Note that the 2 hooks and the shell may be of any length, dimension, material, and design. Note that the 2 hooks may be of different lengths/heights. Note that the bent portions of the hooks may be at different levels or the same level. Note that the distal needle ends of the 2 hooks may be at different levels or the same level. Note that the proximal ends of the 2 hooks may be controlled or rotated or locked or unlocked by any mechanical, electromagnetic, electric, or other means or any design. These proximal controls may be rotated or controlled independently or dependently of each other.

FIG. 6B illustrates the center piece of the second variation of the invention (the "inside-out" variation). It consists of a pair of J- or U-shaped (inverted) hooks (1 and 2) whose sharp distal ends (3 and 4) can be attached to the ends of a suture strand. The shafts of the 2 hooks (1 and 2) may be accommodated within the lumen of a elongated shell (5). The shell may be absent in other embodiments. The shell may have a tapered distal end (6), which may have a slit (shown in the present embodiment) or other types of suture strand carrying mechanism (7). The suture strand carrying mechanism may be a simple slit at one side of the distal shell wall, clip, hole, spring-loaded grasper, . . . etc, encompassing any type of mechanical, electromagnetic, electrical, or other means and any type of dimension and design. This suture carrying mechanism may be located at any part of the center piece of the device. Rotation (clockwise or counter clockwise) of the proximal ends of the hooks (8 and 9), associated with the proximal end of the shell, leads to the rotational movements of the hooks (that is, rotation along their respective longitudinal axis—therefore, the distal ends of the hooks may be positioned inside or outside the shell lumen by rotating their respective proximal ends). In FIG. 6B, the distal needle ends of the hooks (3 and 4) are rotated inward towards each other and, therefore, are inside the shell (5). Note that the 2 hooks and the shell may be of any length, dimension, material, and design. Note that the 2 hooks may be of different lengths/heights. Note that the bent portions of the hooks may be at different levels or the same level. Note that the distal needle ends of the 2 hooks may be at different levels or the same level. Note that the proximal ends of the 2 hooks may be controlled or rotated or locked or unlocked by any mechanical, electromagnetic, electric, or other means or any design. These proximal ends may be controlled or rotated independently or dependently of each other.

Figure 6E:
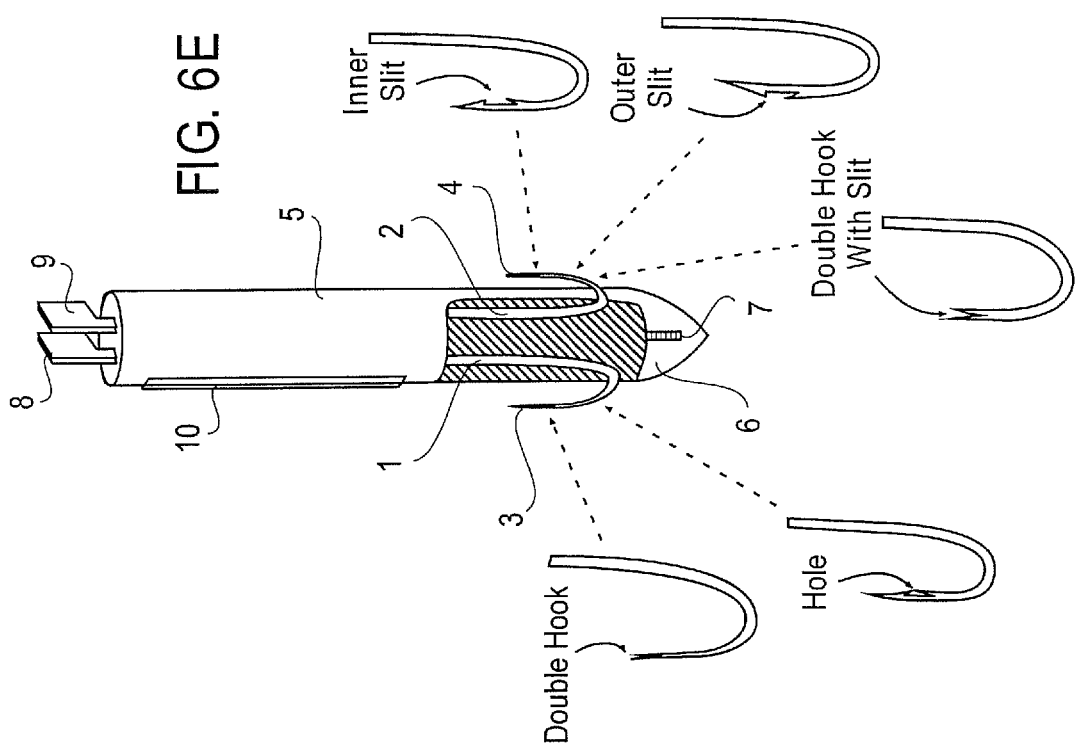
Figure 6C:
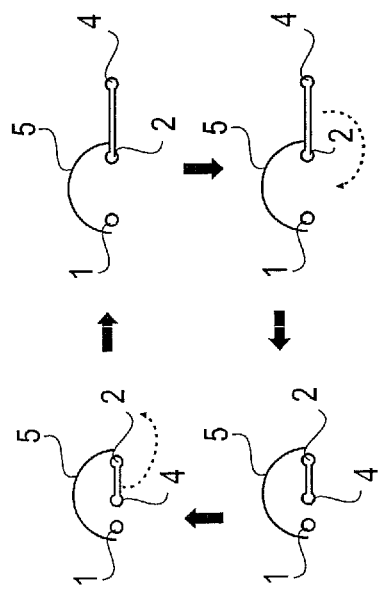

FIG. 6C illustrates the rotational movements of one of the hooks. By rotating the proximal end of hook shaft (2) along its longitudinal axis, its distal end (4) is rotated away from the other hook shaft (1) and becomes outside of shell wall (5). Rotating the same hook shaft (2) along its longitudinal axis in the opposite direction allows its distal end (4) to return to the lumen of the shell. The 2 hooks may be rotated independently of each other in some embodiments (as shown in FIG. 6C) but may be rotated synchronously via a central control mechanism in other embodiments.

Figure 6D:
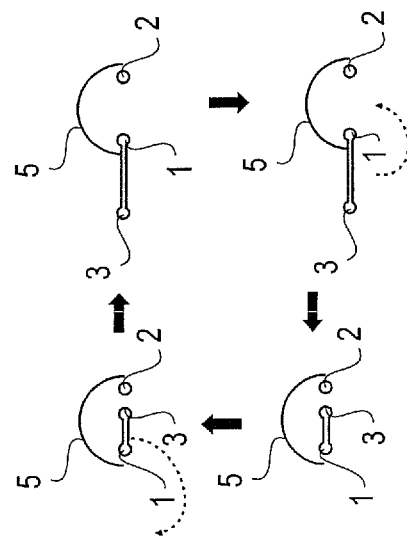

FIG. 6D illustrates the rotational movements of one of the hooks. By rotating the proximal end of hook shaft (1) along its longitudinal axis, its distal end (3) is rotated away from the other hook shaft (2) and becomes outside of shell wall (5). Rotating the same hook shaft (1) along its longitudinal axis in the opposite direction allows its distal end (3) to return to the lumen of the shell. The 2 hooks may be rotated independently of each other in some embodiments (as shown in FIG. 6D) but may be rotated synchronously via a central control mechanism in other embodiments.

FIG. 6E is a 3-dimensional illustration of the center piece of the "inside-out" variation of the invention. It consists of a pair of J- or U-shaped (inverted) hooks (1 and 2) whose sharp distal ends (3 and 4) can be attached to the ends of a suture strand. The shafts of the 2 hooks (1 and 2) may be accommodated within the lumen of a elongated hollow shell (5). The shell may be absent in certain embodiments. The shell may have a tapered distal end (6), which may have a slit (shown in the present figure) or other types of suture strand carrying mechanism (7). The suture strand carrying mechanism may be a simple slit at one side of the distal shell wall, clip, hole, spring-loaded grasper, . . . etc, encompassing any type of mechanical, electromagnetic, electrical, or other means and any type of dimension and design. This suture carrying mechanism may be located at any part of the center piece of the device. Rotation (clockwise or counter clockwise) of the proximal ends of the hooks (8 and 9), associated with the proximal end of the shell, leads to the rotational movements of the hooks (that is, rotation along their respective longitudinal axis—therefore, the distal ends of the hooks may be positioned inside or outside the shell lumen by rotating their proximal ends). The proximal controls of the hooks (8 and 9) may be based on any mechanical, electromagnetic, electrical, or other design or means, and they may be rotated or controlled independently or dependently. In FIG. 6E, the distal needle ends of the hooks (3 and 4) are rotated outward and 180 degrees away from each other and, therefore, are outside the shell (5). The figure also illustrates a protruding ridge or guide (10) associated with the exterior surface of the center piece shell wall (5). This protruding design may be present in some embodiments but absent in others, and this may be accommodated by the slit of the outer shell component of the invention (see FIG. 7)—to prevent the rotation of the center piece within the lumen of the outer shell component. Note that rather than having a protruding design, other embodiments may have a concave design such as groove or slit. The inset pictures illustrate various methods and designs involved in the attachment of a suture strand end to the distal end/needle tip of a hook of the center piece. Slits, holes, double-hook with slit, . . . etc and any type of mechanical, electromagnetic, electrical, and other means and design may be used to attach the end of a suture strand to the distal end of each of the 2 hooks in the invention.

In certain embodiments without the shell (present and shown in 6A-6D), the needle rotational directions may be different from those illustrated in FIGS. 6C-6D. One such embodiment is shown in FIG. 6F. This variation consists of a pair of J-shaped or U-shaped (inverted) hooks (1 and 2) whose sharp distal ends (3 and 4) can be attached to the ends of a suture strand. The shafts of the 2 hooks (1 and 2) may be accommodated within the lumen of an elongated cylindrical shell (5). (Note that the shell may be absent in certain embodiments.) The bottom surface of the hooks are connected to a suture-carrying (or storage) entity (7) with a tapered distal end (6), and the suture strand carrying mechanism may be of any type or design. The suture-carrying entity (7) may be hollow (to house or store suture strand) or solid in nature. When the hooks are rotated in such a way that the needle points (3 and 4) are within the boundary of outer shell (5), as in diagram (A), the 2 halves of the suture-carrying entity (7) come together to provide a housing compartment for suture strand storage. When the hooks are rotated in such a way that the needle points (3 and 4) are 180 degrees away from each other and are outside the boundary of the outer shell (5), as in diagram (B), the 2 halves of the suture-carrying entity (7) are separated from each other, allowing the housed suture strand to be detached from the suture-carrying entity (7). Note that the 2 hooks and the shell may be of any length, dimension, material, and design. Note that the 2 hooks may be of different lengths/heights. Note that the bent portions of the hooks may be at different levels or the same level. Note that the distal needle ends of the 2 hooks may be at different levels or the same level. Note that the proximal ends of the 2 hooks (8 and 9) may be controlled or rotated or locked or unlocked by any mechanical, electromagnetic, electric, or other means or any design. These proximal ends may be controlled or rotated independently or dependently of each other. These 2 ends may be controlled via a central dial or mechanism to facilitate the use of the present invention. Diagram (C) illustrates the rotational movements of the hooks. By rotating the proximal end of hook shaft (2) along its longitudinal axis, its distal end (4) is rotated away from the other hook shaft (1) and becomes outside the boundary of shell wall (5). By rotating the proximal end of hook shaft (1) along its longitudinal axis, its distal end (3) is rotated away from the other hook shaft (2) and becomes outside the boundary of shell wall (5). Rotating the same hook shaft (2) along its longitudinal axis in the opposite direction allows its distal end (4) to return to the luminal boundary the shell (5). Rotating the same hook shaft (1) along its longitudinal axis in the opposite direction allows its distal end (3) to return to the luminal boundary of the shell (5). The 2 hooks may be rotated independently of each other in some embodiments (as shown in FIG. 6F) but may be rotated synchronously via a central control mechanism in other embodiments.

FIG. 7A illustrates one variation of the 3-dimensional and cross-sectional views of the outer shell component of the "inside-out" variation of the invention. The shell body (11) has a lumen (12) and a slit along its longitudinal axis (13). The slit may be absent in certain embodiments. There are 2 wings attached to its distal end (14 and 15). The wings have portions without hollow space or lumen (16 and 17). The 2 wings also have portions with lumen (18 and 19). The 2 wings are attached to the distal portion of the outer shell, and the attachment may be achieved via any mechanical, electrical, electromagnetic, or other means or any design. In the figure, there are slits in the flaps (22 and 23, which represent the continuation of the outer shell wall) at the distal portion of the outer shell, and these 2 slits accommodate the body of the wings. Any component of the outer shell component and its associated parts may be of any material, dimension, configuration, or design. In one preferred embodiment, the outer shell component is flexible enough to allow compression towards its central lumen as its side walls are squeezed with manual pressure.

FIG. 7B illustrates that the portions of the wings without lumen (16 and 17) may be attached to the exterior wall of the outer shell component of the invention (11). Such attachment may be achieved via any mechanical, electrical, electromagnetic, or other means or any design. In the figure, the flaps with slits (22 and 23, with 22 not shown) accommodating the wings are bent or folded so that the portions of the wings without lumen (16 and 17) are attached to the exterior wall of the outer shell. (In this orientation, the portions of wings with lumen—18 and 19—are turned outward 180 degrees away from each other and become perpendicular to the longitudinal axis of the outer shell component). Inset 1 shows that the attachment is achieved via a male-female connection: with a protruding component located on exterior wall of outer shell (20) that can be accommodated by and locked into a hole on the each of the portions of the wings without lumen (16 and 17, with 17 not shown). Inset 2 shows that the attachment is achieved via a ring external to the outer shell (11), accommodating the outer shell circumference as well as both wings (at the level of the portions of wings without lumen—16 and 17, with 17 not shown). Alternatively, in some embodiments, there may be a rigid (such as c) ring that is integrated as part of the outer shell wall and has attachment means (any type) for the portions of wings without lumen, which is not shown in the figure. (Such rigid ring may ensure that the 2 wings are positioned symmetrically at the same level in relation to the outer shell component.) Note that any component of the outer shell component (such as the shell wall and the wings) may be of any dimension, configuration, material, and design. In one preferred embodiment, the outer shell is flexible enough to be compressed against its lumen (12) as its side walls are squeezed with manual pressure.

FIG. 7C illustrates another variation of the component described in FIG. 7B, in which the portions of the wings without lumen (16 and 17) may be attached to the exterior wall of the outer shell component of the invention (11). In this variation (7C), the slit (13) is absent and is replaced by a groove (G) along the inner wall of the outer shell component (11). The labels that are used in FIG. 7B, such as 12, 20, 16, 23, 18, and 19, also apply to FIG. 7C.

FIG. 8A illustrates an obturator (or a guide) that can be accommodated by the hymen of the outer shell component of the invention (the "inside-out" variation). It can also be accommodated by the lumen of a laparoscopic trocar. The obturator may be of any dimension, configuration, material, or design. In one preferred embodiment, its body (24) is hollow and compressible (towards its lumen as the side walls are squeezed by manual pressure). However, such feature may be absent in certain embodiments, in which the body (24) is rigid (or even non-compressible) and may be solid in nature. It may have a tapered distal end to facilitate its insertion into the trocar wound site (25).

FIG. 8B illustrates that the obturator is placed within the lumen of the outer shell component in a 3-dimensional view. Obturator body (24), obturator distal end (25), outer shell body (11), outer shell slit (13), outer shell flaps with slits accommodating the wings (23 and 22, with 22 not shown), 2 wings with portions without lumen (16 and 15) and portions with lumen (18 and 19). Note that a protruding mechanism (male part) is present on the outer shell side wall (20, with its counterpart 180 degrees away and not shown), which can be accommodated by and locked into the "locking hole of the wing" (located at the portion of the wing without lumen on each side). Note that the obturator (24) can be accommodated with the lumen of the outer shell component (11), and these 2 structures may be locked (and unlocked) to each other via any mechanical, electromagnetic, electrical, or other means and any design. Furthermore, there may be valves or other gas-leak prevention means or design for the outer shell and/or obturator to minimize the risk of gas leak during the removal of the obturator from the outer shell lumen (see FIG. 9F below).

FIG. 9 (9A-9L) illustrates one possible method of deploying the second variation (the "inside-out" variation) of the invention to close a trocar wound.

FIG. 9A is a cross-sectional view of the trocar wound site of the abdominal wall, showing skin (S), subcutaneous tissue layer (ST), external layer of fascia (F) providing strength to body wall, muscle (M), and peritoneum (P). The abdominal cavity space (AC) is below the level of peritoneum (P). These labels apply to the remaining figures under FIG. 9. A laparoscopic trocar (T) is also shown at the trocar wound site.

FIG. 9B illustrates the placement of the obturator into the lumen of the trocar (T). Proximal part of the obturator body (24) is outside the trocar, and the tapered distal end of the obturator (25) is associated with the distal end of the trocar.

FIG. 9C illustrates the removal of the trocar from the wound site while the obturator (24) is left in place.

FIG. 9D illustrates the insertion of the outer shell component of the device along the obturator towards the wound opening. Outer shell body (11) with its lumen accommodates the body of the obturator (24). Distal obturator end (25), the portions of wings without lumen (15 and 16), and the portions of wings with lumen (18 and 19) are also shown. (Note that in certain embodiments, the obturator (24) may be inserted through the lumen of the outer shell body (11) first before the removal of the trocar from the wound site. In this alternative method with the obturator-outer shell assemble—in which the steps illustrated in FIGS. 9B-9D are not applicable—the obturator tapered end (25) is first placed into the wound site after trocar removal. The outer shell component of the device is then placed along the obturator into the wound opening.)

FIG. 9E illustrates the rotation of the wings at their attachments to the outer shell distal portion so that the portions of the wings with lumen (18 and 19) are inserted into the subcutaneous tissue layer. Note that the portions without lumen are locked to the exterior wall of the outer shell (11) at specific sites (20). In the present figure, the male-female locking mechanism is shown, with a protruding mechanism on the exterior wall of outer shell (20). Obturator (24) is still inside the outer shell (11).

FIG. 9F shows the same setup as that in FIG. 9E, except that the obturator has been removed from the surgical site. The labels used in FIG. 9E also apply to the present figure.

FIG. 9G shows the insertion of the center piece of the device into the lumen of the outer shell component (11). Note that the center piece is loaded with a strand of suture attached to the distal needle ends of the hooks (3 and 4). The 2 hooks (1 and 2) turned towards each other and accommodated within the lumen of its shell, their distal sharp ends (3 and 4) carrying the ends of the suture strand, proximal controls of the hooks (8 and 9), distal tapered end of central piece (6) with suture securing/carrying mechanism (7), the portions of wings without lumen (15 and 16), and the portions of wings with lumen (18 and 19) are also shown. The wings are also locked to the exterior wall of the outer shell component via a locking mechanism (20).

FIG. 9H shows that the 2 hooks (1 and 2) are rotated outward and become 180 degrees away from each other (by rotating their respective proximal controls—8 and 9), now with their distal tips (3 and 4) outside its center piece shell. Note that the center piece is loaded with a strand of suture attached to the distal needle ends of the hooks (3 and 4). The outer shell component wall (11), the proximal controls of the hooks (8 and 9), distal tapered end of central piece (6) with suture securing/carrying mechanism (7), the portions of wings without lumen (15 and 16), and the portions of wings with lumen (18 and 19) are also shown. The wings are also locked to the exterior wall of the outer shell component via a locking mechanism (20).

FIG. 9I shows that the center piece device with its 2 hooks (1 and 2, pointing 180 degrees away from each other and carrying the ends of a suture strand) is pulled up against the abdominal wall, leading to full-thickness penetration of all layers of the abdominal wall (from peritoneum to skin) by the 2 hook needle ends (3 and 4) attached to the ends of a suture strand. The outer shell component wall (11), the portions of wings without lumen (15 and 16), and the portions of wings with lumen (18 and 19) remain in the same position at the wound site while the center piece is being pulled upward towards the body wall to deliver the 2 ends of the suture strand to the space outside the skin. The wings are locked to the exterior wall of the outer shell component via a locking mechanism (20). Distal tapered end of central piece (6) with suture securing/carrying mechanism (7) are also shown. Note that the needle tips of the 2 hooks (3 and 4) also travel through the hollow spaces (lumen) of the 2 wings (18 and 19) positioned in the subcutaneous layer during this step.

Figure 9J:
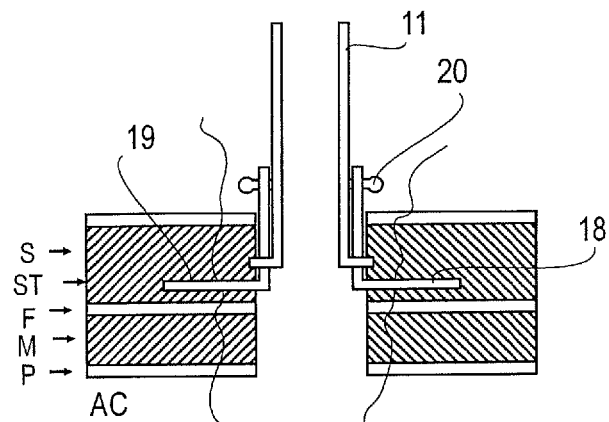

FIG. 9J shows the suture path after the removal of the center piece of the device. Following step in FIG. 9I, the 2 ends of the suture strand are detached from the needle tips of the 2 hooks and secured outside the skin. The center piece device is then reinserted back into the abdominal cavity, after which the hooks are rotated towards each other via their proximal controls, followed by the removal of the center piece of the device. The suture path is now as follows: the suture originates from the space outside the skin, travels through all layers of the abdominal wall (from skin to peritoneum) as well as the lumen of the first wing of the device (19), enters abdominal cavity, exits abdominal cavity, travels through all layers of abdominal wall (from peritoneum to skin) and the lumen of the second wing of the device (18), and enters the space outside the skin. The wings are locked to the exterior wall of the outer shell component (11) via a locking mechanism (20).

Figure 9K:
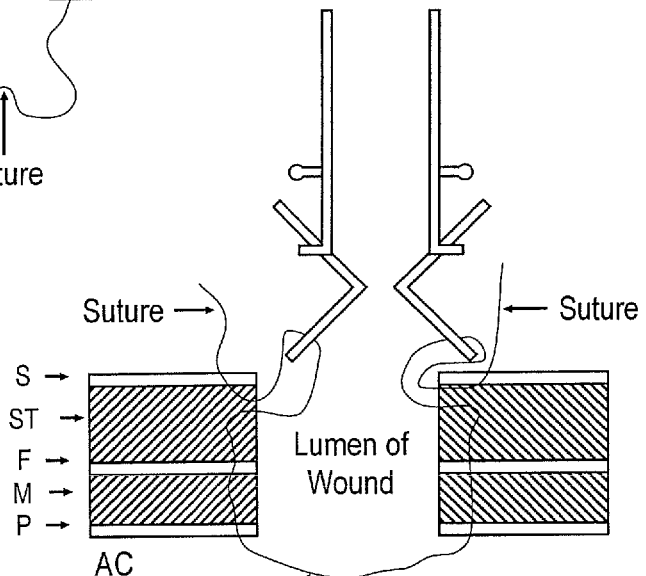

FIG. 9K shows the removal of the remaining device from the wound site. During this maneuver, the portions of the suture strand outside the skin are pulled into the subcutaneous tissue layer and the lumen of the wound.

Figure 9L:
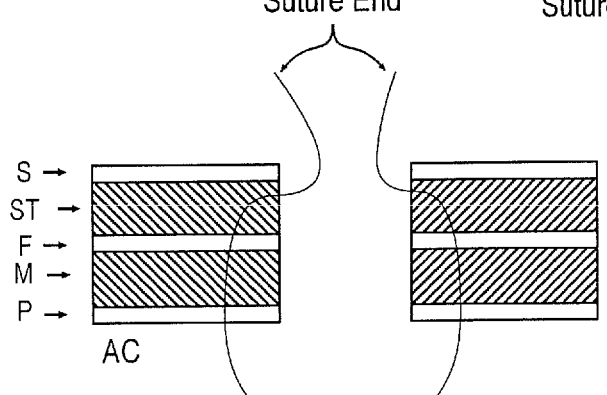

FIG. 9L shows the path of the single suture strand at the wound site after the removal of the device. Note that the suture travels through all layers of the abdominal wall below the skin level (including fascia and peritoneum), enters the abdominal cavity space, exits the abdominal cavity space, and travels through all layers of the abdominal wall below the skin level (including peritoneum and fascia). The 2 ends of the suture strand can then be tied to each other for wound closure. Note that skin is not incorporated into the wound closure.

DETAILED DESCRIPTION OF EMBODIMENTS

Various embodiments are shown in the figures attached. There are 2 main variations of the present invention. The first variation—the "outside-in" variation—is shown in the earlier figures (FIGS. 1-5). The second variation—the "inside-out" variation—is shown in the latter figures (FIGS. 6-9).

The fundamental principle shared by all variations and embodiments of the present invention is that there is at least 1 ring (equivalent to "wing portion with lumen" in all the figures illustrated for the invention) placed into the subcutaneous tissue layer (between skin and fascia) so that suture passage through all layers of the abdominal wall (including skin, subcutaneous tissue layer, fascia, muscle, and peritoneum), regardless of the direction of passage (from the space outside the skin towards abdominal cavity space or from the abdominal cavity space towards the space outside the skin), allows capture of all tissue layers of the abdominal wall except the skin following the removal of the ring from the subcutaneous tissue layer. This is due to the fact that the portion of the suture strand outside the skin is pulled into the subcutaneous tissue layer and the lumen of the wound site during the removal of the ring from the wound site. (In other words, the result is that the suture strand travels through the subcutaneous tissue layer, fascia, muscle, and peritoneum, into the abdominal cavity space, exits the abdominal cavity space via the lumen of the wound). When a single ring is used on both sides of the wound lumen (asynchronously—shown in FIG. 5) or when 2 separate rings are used for the wound site synchronously (shown in FIGS. 4 and 9), suture closure incorporating all body wall layers (other than the skin) can be achieved.

In one preferred embodiment, the first variation of the device consists of 3 main components: a center piece with its 2 wings, a ring piece, and a suture passer. Any part of each of the 3 components may be made from any material, dimension, and design. Any of the 3 components may be integrated into another component(s) in other embodiments. In another preferred embodiment, the center piece has a lumen that accommodates a tubular rod with 2 distal wings (as in FIGS. 4O and 4P) that carry 2 terminal ends of the suture strand.

The details of some of the embodiments of the first variation of the device have been described in FIGS. 1-5.

In one preferred embodiment, the second variation of the device consists of 3 main components: a center piece with its 2 inverted hooks (carrying the 2 ends of a suture strand), an outer shell with its 2 wings, and an obturator. Any part of each of the 3 components may be made from any material, dimension, and design. Any of the 3 components may be integrated into another component(s) in other embodiments.

The details of some of the embodiments of the second variation of the device have been described in FIGS. 6-9. The detailed discussion of the major steps involved in the device deployment is shown in FIG. 9. Note that in certain embodiments, the obturator (24 in FIG. 9) may be inserted through the lumen of the outer shell body (11 in FIG. 9) first before the removal of the trocar from the wound site. In this alternative method with the obturator-outer shell assembly—in which the steps illustrated in FIGS. 9B-9D are not applicable—the obturator tapered end (25 in FIG. 9) is first placed into the wound site after trocar removal. The outer shell component of the device is then placed along the obturator and inserted into the wound opening In certain embodiments the device (including both "outside-in" and "inside-out" variations) is designed to have disposable elements or to be entirely disposable. Disposability is really a function of cost in relation to expense of sterilization. Heat and chemical sterilization is a relatively inexpensive process, but it may damage certain or the more delicate elements of an apparatus. Any component of the device (including variations) may be made disposable or reusable. In other embodiments, the entire device may be disposable, dispensing with the need for sterilization altogether.

Any component and any associated part of the 2 variations of the invention may be made from any material, with any dimension, configuration, rigidity or flexibility, and design. The attachment and association means between and among the different components or parts may be achieved mechanically, electromagnetically, electrically, or any other method.

The invention is designed primarily to close lap aroscopic trocar wound sites. It may also be used for other types of applications in surgery (such as hernia repair) or body systems including the chest cavity. The principle of a strand of suture or string passing through a ring outlined above may be applicable to other medical and non-medical fields, all of which should be encompassed by the present invention.

It should be also be noted that in the first variation of the device ("outside-in" variation), the center piece may have one or more associated wings. Two wings represent one preferred embodiment, although other embodiments may have 1, 3, 4, or more wings.

It should also be noted that in the second variation of the device ("inside-out" variation), the outer shell component may have one or more associated wings with lumen. Two wings represent one preferred embodiment, although other embodiments may have 1, 3, 4, or more wings.

It should also be noted that in the second variation of the device ("inside-out" variation), the center piece component may have one or more associated hooks with lumen. Two hooks represent one preferred embodiment, although other embodiments may have 1, 3, 4, or more wings. It should also be noted that the inverted hook may have a configuration other than inverted U (which is one preferred embodiment), although J, L, . . . etc and other variations at various angles (relative to the longitudinal axis of the hook shaft) to allow the needle tip point towards the proximal control of the respective hook may be present in other embodiments.

In any of the wings with lumen (in both first and second variations of the invention), the wing tips may be sharp, blunt, tapered, or others in design and configuration. The dimension of each wing lumen may be of any design. The wings may be of any material, dimension, and design.

In all parts of the present document including claims, the wings with lumen (present in both the "inside-out" and "outside-in" variations of the invention) through which the suture passer or needle carrying the suture strand travels through should be considered as a form of rings (defined as a element with circumferential enclosure and central lumen allowing passage of other elements). In other words, the wings with lumen are specific forms of rings.

The present invention provides various advantages over the prior art devices and methods. It provides full-thickness closure of a small laparoscopic wound site, capturing all body wall tissue layers, except the skin, on both sides of the wound lumen. It provides such closure in a simple, easy-to-use, reliable, and fast manner. The second variation of the invention ("inside-out" variation), in fact, allows the surgeon to complete wound closure without much of the assistant's help—the assistant only needs to control the laparoscope and help the surgeon visualize the trocar wound site from the intra-abdominal perspective. Additionally, the present invention is simple and inexpensive to manufacture, simple to use and robust in use, and can be used with a variety of wound dimensions and depths.

It will be readily appreciated that various adaptations and modifications of the described embodiments can be configured without departing from the scope and spirit of the invention and the above description is intended to be illustrative, and not restrictive, and it is understood that the applicant claims the full scope of any claims and all equivalents.

The invention claimed is:

1. A device for closing a skin layer, a subcutaneous layer and a fascia layer of a trocar opening in the abdominal wall, the device comprising:
   an elongate member having a proximal end with a proximal end diameter and a distal end with a distal end decreasing diameter such that the distal end diameter is largest at the intersection with the proximal end, wherein the maximal distal end diameter is greater than the proximal end diameter;
   a first rod member attached substantially perpendicularly to a first wing member to form a first elbow at a constant angle, the first elbow pivotally attached to a first location on the elongate member at the proximal end, the first wing having a lumen;
   a second rod member attached substantially perpendicularly to a second wing member to form a second elbow at a constant angle, the second elbow pivotally attached to a second location on the elongate member at the proximal end, the second wing having a lumen; and a removable ring member having a center lumen and suture passer tunnels
   wherein the device is configured such that when the first and second rod members are in a position substantially perpendicular to the elongate member, the first and second wing members are substantially parallel to the elongate member at the proximal end, and when the first and second rod members are rotated towards the elongate member into a position substantially parallel to the elongate member, the first and second rod members are positioned within the ring member center lumen and the first and second wing members are automatically rotated into a position substantially perpendicular to the elongate member inside the trocar opening such that the first and second wing members are positioned within the subcutaneous tissue layer between the skin and fascia layers of the trocar opening and aligned with the ring member suture passer tunnels.

2. The device of claim 1, wherein the removable ring is configured to accommodate and retain the first and second rod members against the proximal end of the elongate member.

3. The device of claim 1, wherein the alignment of the suture passer tunnels with the first and second lumen allow a suture passer or a string delivery device to pass through.

4. The device of claim 1, wherein the suture passer tunnels of the removable ring member are fixed in position relative to the first and second lumen of the first and second wing members when the removable ring member accommodates the proximal end of the elongate member and the first and second rod members when they are in the vertical position.

5. The device of claim 1, the device comprising at least one additional rod member attached substantially perpendicularly to an additional wing member to form an additional elbow, the additional elbow pivotally attached to an additional location of the elongate member at the proximal end, the additional wing having a lumen.

6. The device of claim 1, wherein the device forms a structure extending across the trocar opening.

7. The device of claim 1, wherein the removable ring member is configured to immobilize the first and second rod members when they are in the vertical position and aligned against the elongate member.

8. A method for closing an opening in a layer of biological tissue comprising:
   a. placing an elongate member into a trocar opening in the layer of biological tissue, the layer of biological tissue having a top edge and a bottom edge;
   b. protruding a wing member into the layer of the biological tissue from a section of the elongate member within the trocar opening, wherein the wing member has a rod member attached substantially perpendicularly to form an elbow having a constant angle, the elbow being pivotally coupled to the elongate member, and wherein the wing member is automatically rotated into a position substantially perpendicular to the elongate member when the rod member is rotated towards the elongate member into a position substantially parallel to the elongate member;
   c. using a suture passer to pass a strand member from the top edge of the layer of the biological tissue, then through the layer of biological tissue, through a lumen of the wing member, and through the second edge of the layer of biological tissue; and
   d. depositing an end of the strand member beyond the bottom edge of the layer of the biological tissue.

9. The method of claim 8 further comprising aligning a suture passer tunnel on a removable ring member and the lumen on the wing member.

10. The method of claim 9, wherein the strand member comprises a string or a suture, the method further comprising inserting a string delivery device or a suture delivery device through the suture passer tunnel of the removable ring member and the lumen of the wing member.

11. The method of claim 8, wherein the strand member comes out from a side wall of the layer of biological tissue into the trocar opening.

12. The method of claim 8, wherein the strand member forms at least a partial circle across the trocar opening.

13. The method of claim 8, wherein a first section of the strand member placed across the trocar opening is substantially parallel to a second section of the strand member.

14. The method of claim 8 further comprising sliding a removable ring member over the rod member, so that the lumen on the wing member is substantially aligned with a suture passer tunnel on the removable ring member.

15. The method of claim 8 further comprising securing the rod member to the elongate member.

16. The method of claim 8, wherein the strand member comprises a string or a suture, the method further comprising inserting a string delivery device or a suture delivery device through the lumen of the wing member.

17. The method of claim 8 wherein the strand member comprises a suture strand.

18. The method of claim 8 further comprising pulling the strand member.

* * * * *